(12) United States Patent
Suh et al.

(10) Patent No.: US 11,071,686 B2
(45) Date of Patent: Jul. 27, 2021

(54) AUTOMATIC CARDIOPULMONARY RESUSCITATION DEVICE AND CONTROL METHOD THEREFOR

(71) Applicant: Seoul National University R&DB Foundation, Seoul (KR)

(72) Inventors: Gil Joon Suh, Seoul (KR); Woon Yong Kwon, Seoul (KR); Kyung Su Kim, Seoul (KR); Sang Hoon Na, Seoul (KR); Jaeheung Park, Yongin-si (KR); Jung Chan Lee, Seoul (KR); Yoon Sun Jung, Seoul (KR); Kyoung Min You, Seoul (KR); Min Ji Park, Seoul (KR); Taegyun Kim, Seoul (KR); Jung-In Ko, Seoul (KR); Jeeseop Kim, Seoul (KR); Jaesug Jung, Seongnam-si (KR); Sanghyun Kim, Seoul (KR); Byeong Wook Yoo, Bucheon-si (KR); Byeongtak Lee, Seoul (KR); Woo Sang Cho, Yongin-si (KR); Jin Woo Choi, Goyang-si (KR)

(73) Assignee: Seoul National University R&DB Foundation, Seoul (KR)

(*) Notice: Subject to any disclaimer, the term of this patent is extended or adjusted under 35 U.S.C. 154(b) by 454 days.

(21) Appl. No.: 16/073,612

(22) PCT Filed: Jan. 26, 2017

(86) PCT No.: PCT/KR2017/000971
§ 371 (c)(1),
(2) Date: Jul. 27, 2018

(87) PCT Pub. No.: WO2017/131477
PCT Pub. Date: Aug. 3, 2017

(65) Prior Publication Data
US 2019/0029919 A1 Jan. 31, 2019

(30) Foreign Application Priority Data

Jan. 29, 2016 (KR) .................. 10-2016-0011876
Dec. 16, 2016 (KR) .................. 10-2016-0172286

(51) Int. Cl.
*A61H 31/00* (2006.01)
*A61B 5/021* (2006.01)
(Continued)

(52) U.S. Cl.
CPC ......... *A61H 31/006* (2013.01); *A61B 5/4836* (2013.01); *A61B 5/0077* (2013.01);
(Continued)

(58) Field of Classification Search
CPC .............. A61H 31/00; A61H 2031/003; A61H 31/006; A61H 2201/1659;
(Continued)

(56) References Cited

U.S. PATENT DOCUMENTS 8,007,451 B2   8/2011   Havardsholm et al.
8,591,423 B2   11/2013  Doron
(Continued)

FOREIGN PATENT DOCUMENTS

CN   1468592 A    1/2004
CN   2645604 Y    10/2004
(Continued)

OTHER PUBLICATIONS

International Search Report issued in corresponding International Application No. PCT/KR2017/000971 dated May 11, 2017, with translation (3 pages).
(Continued)

*Primary Examiner* — Tu A Vo
(74) *Attorney, Agent, or Firm* — Osha Bergman Watanabe & Burton LLP

(57) ABSTRACT

An automatic cardiopulmonary resuscitation device includes a movable chest compressor for repeatedly pressing a
(Continued)

patient's chest at a preset depth and cycle, a cardiac output measurement unit for measuring a cardiac output of the patient in accordance with the pressurization of the chest compressor and a processor for changing pressing locations by performing control such that the chest compressor moves according to a preset method.

9 Claims, 14 Drawing Sheets

(51) Int. Cl.
*A61B 5/08* (2006.01)
*A61B 5/145* (2006.01)
*A61B 5/318* (2021.01)
*A61B 5/00* (2006.01)
*A61B 5/06* (2006.01)

(52) U.S. Cl.
CPC ............ *A61B 5/021* (2013.01); *A61B 5/061* (2013.01); *A61B 5/082* (2013.01); *A61B 5/14542* (2013.01); *A61B 5/318* (2021.01); *A61H 2201/1659* (2013.01); *A61H 2201/1664* (2013.01); *A61H 2201/5007* (2013.01); *A61H 2201/5043* (2013.01); *A61H 2201/5061* (2013.01); *A61H 2201/5089* (2013.01); *A61H 2201/5092* (2013.01); *A61H 2205/084* (2013.01); *A61H 2230/045* (2013.01); *A61H 2230/206* (2013.01); *A61H 2230/208* (2013.01); *A61H 2230/255* (2013.01); *A61H 2230/305* (2013.01); *A61H 2230/65* (2013.01); *A61H 2230/655* (2013.01)

(58) Field of Classification Search
CPC .... A61H 2201/1664; A61H 2201/5007; A61H 2201/5043; A61H 2201/5061; A61H 2201/5089; A61H 2201/5092; A61H 2230/045; A61H 2230/206; A61H 2230/208; A61H 2230/255; A61H 2230/305; A61H 2230/65; A61H 2230/655; A61B 5/4836; A61B 5/0077; A61B 5/021; A61B 5/0402; A61B 5/061; A61B 5/082; A61B 5/14542
See application file for complete search history.

(56) References Cited

U.S. PATENT DOCUMENTS

| | | | |
|---|---|---|---|
| 9,125,793 | B2 | 9/2015 | Palazzolo et al. |
| 9,566,210 | B2 | 2/2017 | Aelen et al. |
| 9,956,135 | B2 | 5/2018 | Stemple |
| 2004/0162587 | A1 | 8/2004 | Hampton et al. |
| 2008/0119766 | A1 | 5/2008 | Havardsholm et al. |
| 2010/0094144 | A1 | 4/2010 | Doron |
| 2010/0114220 | A1 | 5/2010 | Paradis |
| 2010/0198118 | A1 | 8/2010 | Itnati |
| 2013/0218056 | A1 | 8/2013 | Aelen et al. |
| 2014/0342331 | A1 | 11/2014 | Freeman |
| 2015/0182419 | A1 | 7/2015 | Clowdus |
| 2015/0272822 | A1 | 10/2015 | Wik et al. |
| 2015/0366751 | A1 | 12/2015 | Stemple |
| 2016/0058660 | A1* | 3/2016 | Lurie ............... A61G 13/1225 601/41 |
| 2016/0143804 | A1* | 5/2016 | Nilsson ............. A61H 31/006 601/41 |
| 2016/0317385 | A1* | 11/2016 | Salcido ............. A61H 31/006 |
| 2017/0087052 | A1 | 3/2017 | Ma |
| 2017/0156977 | A1* | 6/2017 | Walden ............. A61H 31/006 |

FOREIGN PATENT DOCUMENTS

| | | |
|---|---|---|
| CN | 101002716 A | 7/2007 |
| CN | 102058473 A | 5/2011 |
| CN | 102090973 A | 6/2011 |
| CN | 102119908 A | 7/2011 |
| CN | 103200920 A | 7/2013 |
| CN | 103282009 A | 9/2013 |
| CN | 103735401 A | 4/2014 |
| CN | 104840350 A | 8/2015 |
| CN | 104918594 A | 9/2015 |
| CN | 104970958 A | 10/2015 |
| EP | 2500008 A2 | 9/2012 |
| JP | 2007-307367 A | 11/2007 |
| JP | 2012-504036 A | 2/2012 |
| KR | 2012-0062951 A | 6/2012 |
| KR | 2012-0137135 A | 12/2012 |
| KR | 2014-0119955 A | 10/2014 |
| WO | 2012/075493 A1 | 6/2012 |
| WO | 2015-022387 A1 | 2/2015 |
| WO | 2015/091788 A1 | 6/2015 |
| WO | 2016/081544 A1 | 5/2016 |

OTHER PUBLICATIONS

Written Opinion of the International Searching Authority issued in corresponding International Application No. PCT/KR2017/000971 dated May 11, 2017, with translation (13 pages).
Notification of Grant of Patent for Invention issued in corresponding Chinese Patent Application No. 201780014204.2 dated Apr. 23, 2020, with translation (9 pages).
Extended European Search Report issued in corresponding European Application No. 17744598.8 dated Sep. 19, 2019 (8 pages).
Office Action issued in corresponding Chinese Application No. 201780014204.2 dated Oct. 24, 2019 (17 pages).

* cited by examiner

AUTOMATIC CARDIOPULMONARY RESUSCITATION DEVICE AND CONTROL METHOD THEREFOR

TECHNICAL FIELD

The present disclosure relates to an automatic cardiopulmonary resuscitation device and a control method therefor, and more particularly, to an automatic cardiopulmonary resuscitation device which measures cardiac output and a bio signal, and performs chest compression based on the measured cardia output and bio signal, and a control method therefor.

BACKGROUND ART

Cardiopulmonary resuscitation is an emergency treatment means which is essential when a victim goes into a cardiac arrest or victim's heart is stopped. If the cardiac arrest is not rapidly treated, a brain damage starts after four minutes, and serious damages may be caused in vital organs. In addition, a survival rate is abruptly reduced after 10 minutes. If defibrillation is delayed by 1 minutes, the survival rate may be reduced by 7-10%, but, if cardiopulmonary resuscitation is performed, it is known that the survival rate may be reduced by 2.5-5%. If the cardiopulmonary resuscitation is appropriately performed, the survival rate may be noticeably reduced. However, even a well trained person may be disconcerted when he/she encounters a real cardiopulmonary resuscitation situation, and may not well achieve cardiopulmonary resuscitation.

Even if an emergency medical technician and a hospital medical team, which are good at cardiopulmonary resuscitation, performs cardiopulmonary resuscitation, it may be difficult to continuously provide cardiopulmonary resuscitation of constant quality according to a degree of fatigue, and, if cardiopulmonary resuscitation is performed by a medical team which is not good at cardiopulmonary resuscitation, cardiopulmonary resuscitation of poor quality may be provided. Since cardiopulmonary resuscitation requires a lot of physical energy, the guideline recommends that operators are relieved by each other every 2 minutes. There is a demand for a system which can maintain a depth of at least 5 cm and a speed of 100 times or more per minute according to the recent cardiopulmonary resuscitation guideline, and can increase the chance of a recovery of spontaneous circulation by enhancing coronary pressure by maintaining appropriate cardiac output through sufficient relaxation between compression operations, and can automatically search optimal cardiopulmonary resuscitation to reduce damages to vital organs such as brain, lung, etc., and can provide chest compression continuously without causing fatigue.

As related-art technology for performing chest compression for cardiopulmonary resuscitation, a mechanical automatic chest compression device has been developed, and some products using the same have been introduced. However, these products are manually actuated according to pre-defined compression site, speed, and depth, and thus there is a problem that important parameters for cardiopulmonary resuscitation are not controlled in real time according to a state of a victim.

The background art described above may be owned by the inventors to derive the present disclosure, or is technology information acquired in the process of deriving the present disclosure, and is not necessarily well-known technology published to public before the filing of the present disclosure.

DETAILED DESCRIPTION OF THE PRESENT DISCLOSURE

Technical Objects

An object of the present disclosure is to provide an automatic cardiopulmonary resuscitation device which measures and analyzes cardiac output in real time, and analyzes various bio signal, and determines an optimal chest compression site, and automatically searches optimal values of a site, a cycle, and a depth of compression, and performs chest compression, and a control method therefor.

Technical Solving Method

According to an embodiment, there is provided an automatic cardiopulmonary resuscitation device including: a chest compressor which is movable, and is configured to repeatedly compress a victim's chest to a predetermined depth and in a predetermined cycle; a cardiac output measurement unit configured to measure a cardiac output of the victim caused by compression of the chest compressor; and a processor configured to control the chest compressor to move according to a predetermined method, and to change a compression site, wherein the processor is configured to control the cardiac output measurement unit to measure the cardiac output of the victim at each of the changed compression sites, to select a compression site at which the cardiac output of the victim becomes the maximum, based on the measured cardiac output, and to control the chest compressor to move to the compression site at which the cardiac output of the victim becomes the maximum.

The predetermined method may be a method which measures the cardiac output of the victim while moving the chest compressor in one direction of a horizontal direction or a vertical direction, selects a first compression site at which the cardiac output of the victim becomes the maximum, based on the measured cardiac output, and to move the chest compressor to a second compression site and a third compression site which are on both sides of the first compression site in a direction perpendicular to the moving direction of the chest compressor.

Alternatively, the processor may be configured to select a compression site at which the cardiac output of the victim becomes the maximum as a final compression site, based on cardiac outputs measured at the first to third compression sites.

Alternatively, the processor may be configured to control at least one of a compression site, a compression depth, or a compression cycle of the chest compressor to make the cardiac output of the victim become the maximum.

In addition, the cardiac output measurement unit may be configured to measure the cardiac output of the victim, by using at least one of an ultrasound measurement method, an electrical bioimpedance cardiogram analysis method, capnography, a blood pressure waveform analysis method, or an intracardiac catheter method.

The automatic cardiopulmonary resuscitation device may further include a camera configured to photograph a chest of the victim, and the processor may be configured to determine a compression site of the chest compressor based on an image photographed by the camera.

The automatic cardiopulmonary resuscitation device may further include a sensor configured to measure a pressure of the chest compressor compressing the victim.

The automatic cardiopulmonary resuscitation device may further include a bio signal measurement unit configured to measure a bio signal of the victim, and the processor may be configured to determine whether a current compression site compressed by the chest compressor is an optimal compression site, based on the bio signal measured by the bio signal measurement unit.

The bio signal may include at least one of a blood pressure, an electrocardiogram, end-tidal CO2, or blood oxygen saturation.

According to an embodiment, there is provided a control method of an automatic cardiopulmonary resuscitation device, the method including: repeatedly compressing, by a movable chest compressor (pressure body), a victim's chest at a predetermined initial site to a predetermined depth and in a predetermined cycle; measuring a cardiac output of the victim caused by compression of the chest compressor at the predetermined initial site; measuring the cardiac output of the victim while moving, by the chest compressor, according to a predetermined method, and changing a compression site; and selecting a compression site at which the cardiac output of the victim becomes the maximum, based on the measured cardiac output, and moving the chest compressor to the compression site at which the cardiac output of the victim becomes the maximum.

Advantageous Effect

According to various embodiments, the automatic cardiopulmonary resuscitation device and the control method therefor can select an optimal compression site, and can continuously perform chest compression according to an optimal cycle, depth, or pressure.

In addition, the automatic cardiopulmonary resuscitation device measures and analyzes cardiac output and various bio signals in real time, thereby evaluating the quality of chest compression in real time, and can achieve the best chest compression effect by adjusting a compression site.

Accordingly, a medical team can observe important states of a victim during cardiopulmonary resuscitation, and can focus on providing an appropriate treatment, and therefore, efficiency of treatment of a cardiac arrest can be enhanced. Furthermore, automated cardiopulmonary resuscitation using a robot can be performed in an ambulance or an emergency site as well as hospitals, and thus there is an effect that a survival rate of a victim having a cardiac arrest is noticeably enhanced.

BEST MODE FOR EMBODYING THE INVENTION

Figure 1:
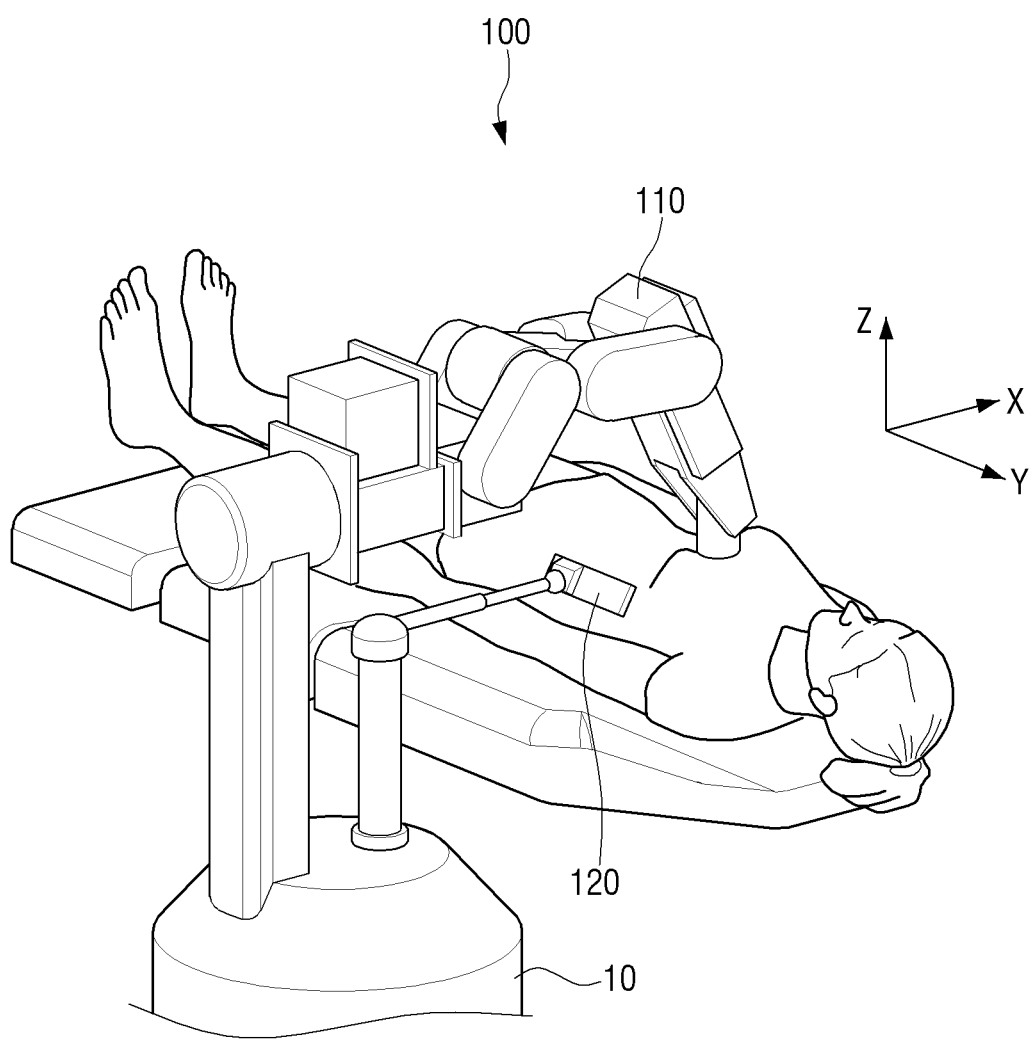
FIG. 1 is a perspective view illustrating an automatic cardiopulmonary resuscitation device according to an embodiment of the present disclosure.

Various embodiments of the present disclosure will be described herein below with reference to the accompanying drawings. Embodiments described in the present disclosure may be variously changed. Specific embodiments are illustrated in the drawings and are described in detail in the detailed descriptions. However, specific embodiments disclosed in the accompanying drawings are merely provided for easy understanding of various embodiments. Therefore, the technical concept of the present disclosure is not limited by specific embodiments disclosed in the accompanying drawings, and should be construed as including all equivalents or alternatives included in the technical concept of the present disclosure and the technical scope.

The term such as "first" and "second" may be used to describe various elements, but the elements are not limited by the above-described terms. These terms may be used for the purpose of distinguishing one element from another element.

The term "include" or "have" used in the exemplary embodiments of the present disclosure indicate the presence of corresponding features, numbers, steps, operations, components, parts described in the present disclosure, or a combination thereof, and do not preclude the presence of one or more other features, numbers, steps, operations, components, parts, or a combination thereof. It will be understood that when an element is "coupled with/to" or "connected with" another element, the element may be directly coupled or connected with/to another element, and there may be an intervening element between the element and another element. To the contrary, it will be understood that when an element is "directly coupled with/to" or "directly connected to" another element, there is no intervening element between the element and another element.

In addition, a "module" or "unit" used in exemplary embodiments performs one or more functions or operations, and may be implemented by using hardware or software or a combination of hardware and software. In addition, a plurality of "modules" or a plurality of "units" may be integrated into one or more modules, except for a "module" or "unit" which needs to be implemented by specific hardware, or may be implemented as one or more processors. As used herein, the singular forms are intended to include the plural forms as well, unless the context clearly indicates otherwise.

In addition, in the following description, detailed descriptions of well-known functions or configurations will be omitted since they would unnecessarily obscure the subject matters of the present invention.

Figure 2:
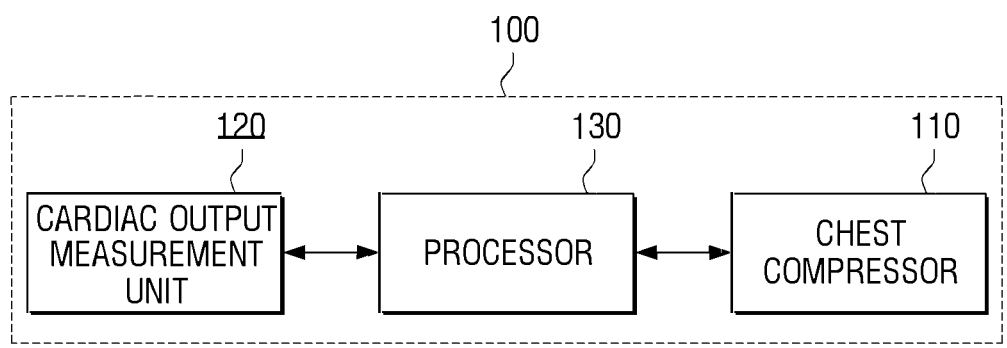
FIG. 2 is a block diagram of the automatic cardiopulmonary resuscitation device according to an embodiment of the present disclosure.

FIG. 1 is a perspective view illustrating an automatic cardiopulmonary resuscitation device according to an embodiment of the present disclosure, and FIG. 2 is a block diagram of the automatic cardiopulmonary resuscitation device according to an embodiment of the present disclosure.

The automatic cardiopulmonary resuscitation device 100 includes a chest compressor 110, a cardiac output measurement unit 120, and a processor 130. The processor 130 may be included in a main body 10 of the automatic cardiopulmonary resuscitation device 100. According to an embodiment, the main body 10 may be implemented in various forms, and may include an input interface (not shown) to receive a user's command. For example, when the input interface receives information from the user, the processor 130 may control the operation of the automatic cardiopulmonary resuscitation device 100 to correspond to the inputted information. The input interface may include a mechanical inputting means (or a mechanical key, a button, a dome switch, a jog wheel, a jog switch, etc.) or a touch type inputting means. According to an embodiment, the touch type inputting means may include a virtual key displayed on a touch screen through software processing, a soft key, or a touch key which is arranged on a portion other than the touch screen.

Alternatively, the main body 10 may include an output interface (not shown) to output measurement information measured at the cardiac output measurement unit 120, measurement information measured at various other sensors or measurement units, etc. For example, the output interface is for generating an output related to sight, hearing, or touch, and may include a display, a speaker, or etc. The display may be implemented as a touch screen by forming an interlayer structure with a touch sensor or being integrally formed therewith. The touch screen may perform the function of the input interface and the function of the output interface, simultaneously, between the automatic cardiopulmonary resuscitation device 100 and the user.

The chest compressor 110 is movable and repeatedly compresses a victim's chest to a predetermined depth and in a predetermined cycle (or at predetermined speed). The chest compressor 110 may include a compression rod of a predetermined area to compress the victim's chest. The chest compressor 110 may be disposed over an upper section of a bed on which the victim is lying, and may compress the victim's chest by a predetermined pressure to a predetermined depth in a predetermined cycle. According to an embodiment, the chest compressor 110 may have a shape similar to a robot arm, and is movable in horizontal and vertical directions, and is rotatable. Alternatively, the chest compressor 110 may change a compression site by moving in an X-axis direction or a Y-axis direction by means of a moving means such as a rail, etc. That is, the chest compressor 110 may find an optimal compression site at which the cardiac output becomes the maximum, and may move to the optimal compression site under control of the processor 130. In addition, the chest compressor 110 may compress the victim's chest by a predetermined pressure to a predetermined depth in a predetermined cycle, while vertically moving over the optimal compression site in a Z-axis direction. In the present disclosure, a straight line connecting the victim's foot and head is defined as the X-axis, a straight line connecting the victim's left side and right side is defined as the Y-axis, and a straight line connecting the victim's chest and the front is defined as the Z-axis. Accordingly, the X-axis direction refers to a foot direction or a head direction of the victim, the Y-axis direction refers to a leftward direction or a rightward direction of the victim, and the Z-axis direction refers to a direction of compressing the victim's cheat from the front or a direction of releasing.

The cardiac output measurement unit 120 measures victim's cardiac output caused by the compression by the chest compressor 110. The cardiac output measurement unit 120 may be connected with the main body separately from the chest compressor 110, or may be connected with the main body integrally with the chest compressor 110. The cardiac output refers an amount of blood ejected from the victim's heart, that is, the ventricle of the heart, for 1 minute. Specifically, the heart repeatedly contracts and expands in a predetermined cycle, and performs a pump function of ejecting blood to the arteries. The pump function may be displayed by the amount of blood ejected for 1 minute, and this is referred to as cardiac output. Alternatively, the pump function may be expressed by minute volume. The cardiac output is determined by a product of the amount of blood ejected by one contraction and the number of times of contracting for 1 minutes (heart rate), and the unit of cardiac output is ml.

The cardiac output may be measured in various methods. For example, an ultrasound measurement method may be used. The ultrasound measurement method measures cardiac output by using echocardiography, aorta ultrasound, transesophageal echocardiography, a doppler monitoring device, or the like. Specifically, the echocardiography is a method for observing a movement of the heart in real time by using ultrasonography. When the chest compressor 110 compresses the victim's chest, the victim's ventricle repeatedly contracts and expands in response to the compression by the chest compressor 110. An area of the contracting and expanding ventricle varies according to a compression site of the chest compressor 110. When the ventricle contracts and expands to the maximum, the cardiac output becomes the maximum. That is, the echocardiography is a method for measuring cardiac output by measuring the area of the contracting and expanding ventricle. The aorta ultrasound is a method for measuring a blood flow rate of blood ejected from the left ventricle to the aorta according to the compression by the chest compressor 110 by using ultrasound, and the transesophageal echocardiography is a method for measuring cardia output by inserting a probe into the throat in a similar way to endoscopy, and by measuring an area of the contracting and expanding ventricle. The doppler monitoring device is a method for measuring cardiac output by using a frequency change according to a moving speed of blood in the heart.

In addition, the measurement of cardiac output may be performed by an electrical bioimpedance cardiogram analysis method, which uses an electric signal of a cardiac impulse, capnography using partial pressure of end-tidal carbon dioxide (End-tidal CO2: EtCO2), a blood pressure waveform analysis method using a waveform of blood pressure, or an intracardiac catheter method which estimates an amount of blood discharged from the ventricle by putting a catheter to the heart through the carotid or the jugular vein, and by inserting a skeletal substance. In particular, the intracardiac catheter method may be used for a victim having a sudden cardiac arrest during an operation. In addition to these, various other methods for measuring cardiac output may be applied. Accordingly, the cardiac output measurement unit 120 may be implemented as an ultrasound device or a spirometer.

The processor 130 controls the chest compressor 110 to be moved according to a predetermined method, and to change the compression site of the chest compressor 110. In addition, the processor 120 controls the cardiac output measurement unit 120 to measure victim's cardiac output at every changed compression site, and selects a compression site at which the victim's cardiac output becomes the maximum, based on the measured cardiac output. The processor 130 controls the chest compressor 110 to be moved to the compression site at which the victim's cardiac output becomes the maximum. The processor 130 determining the optimal compression site, and moving the chest compressor 110 to the optimal compression site will be described in detail. In addition, the processor 130 controls the cycle, pressure, and depth of the chest compressor 110.

The processor 130 may include all kinds of components capable of processing data. For example, the processor 130 may refer to a data processing component embedded in hardware, and having a circuit physically structured to perform a function expressed by a code or a command included in a program. According to an embodiment, the data processing component embedded in hardware may include a processing device such as a micro-processor, a central processing unit, a processor core, a multi-processor, an application-specific integrated circuit (ASIC), a field programmable gate array (FPGA), etc.

Figure 3:
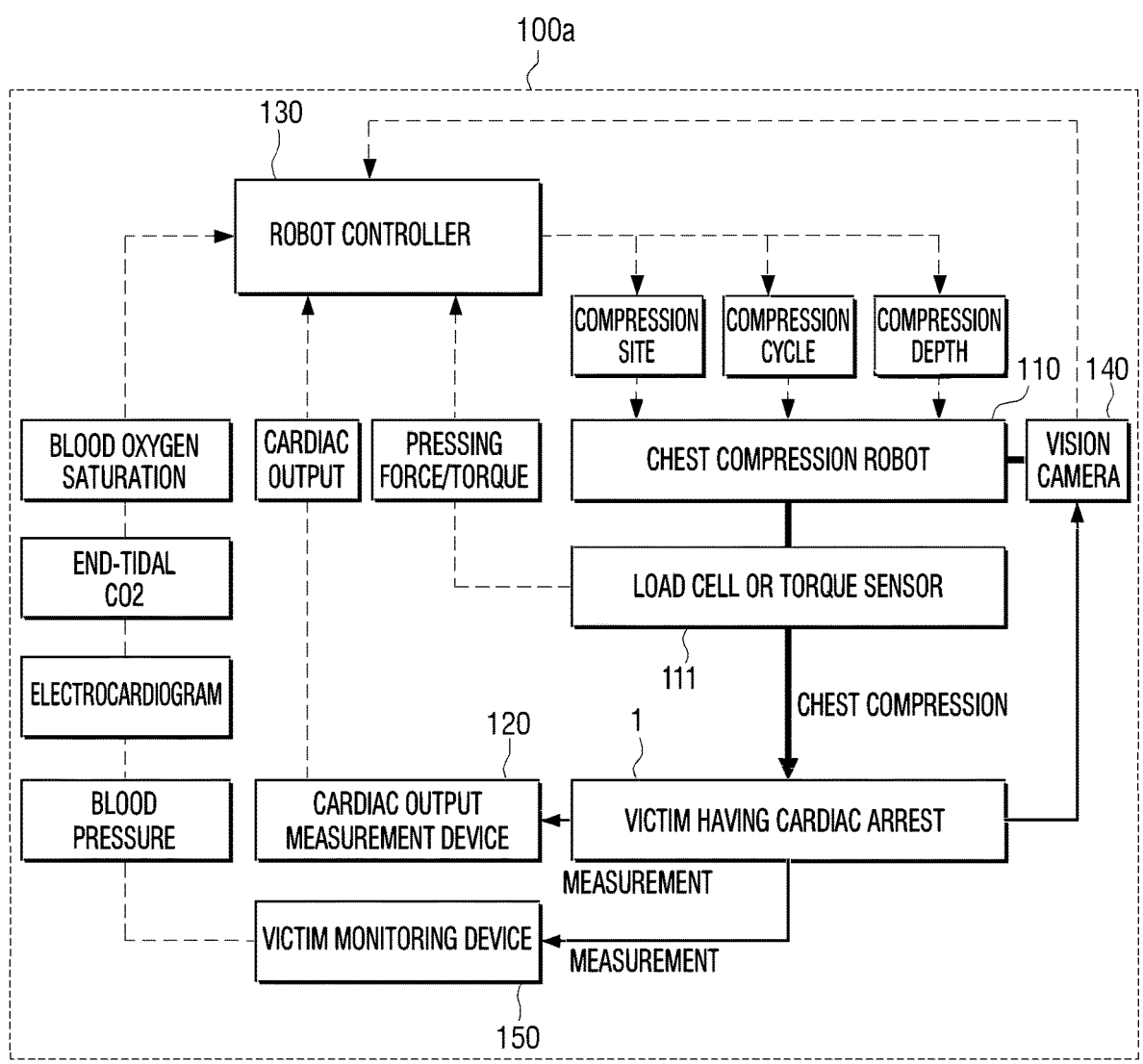
FIG. 3 is a block diagram of an automatic cardiopulmonary resuscitation device according to another embodiment of the present disclosure.

FIG. 3 is a block diagram of an automatic cardiopulmonary resuscitation device according to another embodiment of the present disclosure.

Referring to FIG. 3, the automatic cardiopulmonary resuscitation device 100a may include a chest compression robot 110, a cardiac output measurement device 120, a victim monitoring device 150, a robot controller 130, and a vision camera 140. The chest compression robot 110 of FIG. 3 is the chest compressor 110 of FIG. 2, the cardiac output measurement device 120 of FIG. 3 is the cardiac output measurement unit 120 of FIG. 2, and the robot controller 130 of FIG. 3 is the processor 130 of FIG. 2.

As described above, the robot controller 130 (or processor) may control the chest compression robot 110 (or chest compressor) to compress the chest of a victim 1 having a cardiac arrest at a predetermined compression site to a predetermined compression depth in a predetermined cycle. The cardiac output measurement device 120 (or cardiac output measurement unit) may measure cardiac output caused by chest compression, and may transmit the measured information to the robot controller 130. The robot controller 130 may control the chest compression robot 110 to compress the chest, while changing the compression site according to a predetermined criterion. The cardiac output measurement device 120 may measure cardiac output caused by compression by the chest compression robot 110 at the changed site, and may transmit the measured information to the robot controller 130. The robot controller 130 may determine an optimal compression site based on the transmitted cardiac output information, and may move the chest compression robot 110 to the optimal compression site.

The chest compression robot 110 may include a load cell or torque sensor 111. The load cell or torque sensor 111 may measure a pressure by detecting a value which is changed as a strain gauge is deformed under force or a strain gauge is distorted under force. That is, the load cell or torque sensor 111 may measure the pressure of the chest compression robot 110 to compress the victim's chest. The chest compression robot 110 may transmit information on a force or torque for compressing the chest, which is detected at the load cell or torque sensor 111, to the robot controller 130. The robot controller 130 may determine whether the victim's chest is compressed by an appropriate pressure based on the transmitted information on the pressing force or torque, and may control the compression cycle or the compression depth of the chest compression robot.

The automatic cardiopulmonary resuscitation device 100a may further include the vision camera 140 or the victim monitoring device 150. The vision camera 140 may be disposed on one side of the chest compression robot 110 to photograph an image of the victim's chest or the chest compression robot 110 compressing the victim's chest. In addition, the robot controller 130 may determine a compression site of the chest compression robot 110 based on the image photographed by the vision camera 140. Accordingly, the robot controller 130 may analyze the image photographed by the vision camera 140, and may determine whether the current compression site is the optimal compression site.

The victim monitoring device 150 may measure a victim's bio signal. The victim' bio signal may include a blood pressure, an electrocardiogram, end-tidal CO2, or blood oxygen saturation. The victim monitoring device 150 may be referred to as a bio signal measurement unit. The victim monitoring device 150 (or the bio signal measurement unit) may transmit the measured victim's bio signal to the robot controller 130. The robot controller 130 may analyze the bio signal transmitted from the victim monitoring device 150, may evaluate overall quality of cardiopulmonary resuscitation, and may display the evaluated quality of the cardiopulmonary resuscitation for a medical team. In addition, the robot controller 130 may analyze the bio signal transmitted from the victim monitoring device 150, and may determine whether the current compression site compressed by the chest compression robot 110 is the optimal compression site. That is, the automatic cardiopulmonary resuscitation device 100a may determine the optimal compression site by combining the cardiac output measured by the cardiac output measurement device 120, and at least one bio signal measured by the victim monitoring device 150, and may determine the optimal compression site.

According to an embodiment, the automatic cardiopulmonary resuscitation device 100a may determine the optimal compression site or the quality of the cardiopulmonary resuscitation by using information regarding the measured cardiac output and the end-tidal CO2 (or end-tidal CO2 partial pressure). Alternatively, the automatic cardiopulmonary resuscitation device 100a may determine the optimal compression site or the quality of the cardiopulmonary resuscitation by using information regarding the measured cardiac output, the end-tidal CO2, the blood pressure, the electrocardiogram, and the blood oxygen saturation.

Accordingly, the robot controller 130 of the automatic cardiopulmonary resuscitation device 100a is a kind of central processing unit, and may control an overall process to control the cardiac output measurement device 120 to measure cardiac output and to control the victim monitoring device 150 to measure various bio signals, and to control the compression site, depth, and cycle of the chest compression robot 110 to be in the optimal state, based on the measured cardiac output and the bio signal.

The automatic cardiopulmonary resuscitation device 100a may further include a memory (not shown). The memory may perform a function of storing data processed by the robot controller 130 temporarily or permanently. In addition, the memory may store control software for performing the function of measuring cardiac output at the cardiac output measurement device 120, the function of measuring various bio signals at the victim monitoring device 150, and the function of controlling the compression site, depth, and cycle of the chest compression robot 110 to be in the optimal state, based on the measured cardiac output. In addition, the memory may store various signals and data generated in the automatic cardiopulmonary resuscitation device 100a, for example, the image photographed by the vision camera 140.

For example, the memory may include a storage medium of at least one type of a flash memory type, a hard disk type, a solid state disk (SSD) type, a silicon disk drive (SDD) type, a multimedia card micro type, a memory of a card type (for example, an SD or XD memory, etc.), a random access memory (RAM), a static RAM (SRAM), a read only memory (ROM), an electrically erasable programmable ROM (EEPROM), a programmable ROM (PROM), a magnetic memory, a magnetic disk, and an optical disk. In addition, the automatic cardiopulmonary resuscitation device 100a may further include a communication unit (not shown), and may transmit various data and information to a server or a web storage through the communication unit, and the server or the web storage may store the received data and information.

The automatic cardiopulmonary resuscitation device 100a according to an embodiment of the present disclosure may measure and analyze cardiac output, which indicates the most important state of the heart during cardiopulmonary resuscitation, in real time, and simultaneously, may analyze various bio signals. In addition, the automatic cardiopulmonary resuscitation device 100a may grasp the quality of current cardiopulmonary resuscitation based on the analyzed cardiac output and bio signals, and may automatically search optimal values of the compression site, depth, and cycle, which are the important parameters of cardiopulmonary resuscitation, to provide optimal chest compression, and may automatically control the chest compression robot 110.

Figure 4:
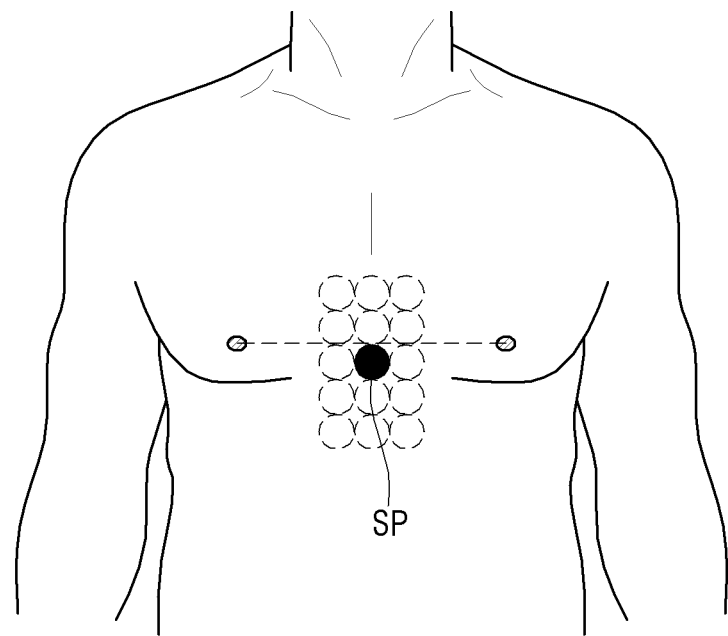
FIG. 4 is a view illustrating an initial site and a movement candidate site for chest compression according to an embodiment of the present disclosure.

FIG. 4 is a view illustrating an initial site and a movement candidate site according to an embodiment of the present disclosure.

Referring to FIG. 4, a chest compression site is illustrated. Initially, the automatic cardiopulmonary resuscitation device 100 starts compressing at a middle point (SP) at which a line connecting victim's both nipples and the sternum meet according to the guideline of the cardiopulmonary resuscitation, as shown in FIG. 4. The initial compression site may be selected by a medical team. Alternatively, when the automatic cardiopulmonary resuscitation device 100 includes the camera 140, the automatic cardiopulmonary resuscitation device 100 may recognize the victim's both nipples as an image by using the camera 140, and may automatically search coordinates of an initial compression starting point on the XY plane. The automatic cardiopulmonary resuscitation device 100 may move down the chest compressor 110 along the Z-axis, and may set a point at which a force is detected by the sensor 111 as an initial compression point.

According to the guideline of the cardiopulmonary resuscitation, the automatic cardiopulmonary resuscitation device 100 starts compressing the chest in a cycle (or speed) of 100-120 times per minute and to a compression depth of 3 cm-5 cm. The cardiac output measurement unit 120 in close contact with the victim measures cardiac output to analyze the quality of cardiopulmonary resuscitation. In addition, when the automatic cardiopulmonary resuscitation device 100 includes the bio signal measurement unit 150, the automatic cardiopulmonary resuscitation device 100 may also measure victim's bio signals, and may analyze the quality of cardiopulmonary resuscitation. The sensor 111 included in the automatic cardiopulmonary resuscitation device 100 may measure a force and a torque, which are generated as a compressing portion of the automatic cardiopulmonary resuscitation device 100 comes into contact with the victim, in real time, and may transmit information on the force and the torque to the processor 130.

The processor 130 may search a compressing condition in which the maximum cardiac output can be derived, based on the cardiac output measured by the cardiac output measurement unit 120, and may control the automatic cardiopulmonary resuscitation device 100. Alternatively, the processor 130 may search an optimal compressing condition in which the maximum cardiac output can be derived, by also considering various bio signals measured by the bio signal measurement unit 150, and may control the automatic cardiopulmonary resuscitation device 100.

The processor 130 may control the cardiac output measurement unit 120 and the bio signal measurement unit 150 to measure cardiac output and bio signals at various points, while moving the chest compressor 110 according to a predetermined criterion. For example, the processor 130 may move the chest compressor 110 by a distance of about 1 cm-2 cm in horizontal and vertical directions. The candidate sites of for chest compression may be 3 points in the horizontal direction by 5 points in the vertical direction, that is, 15 points in total, as shown in FIG. 4. In addition, the candidate sites for chest compression may be 3 points in the horizontal direction by 3 points in the vertical direction, that is, 9 points in total. The moving distance of the chest compressor 110 and the number of candidate points described above are merely examples, and may be variously set.

After searching the compression site, the processor 130 may increase the compression cycle of the chest compressor 110 to acquire additional cardiac output, and, when elastic recovery of the chest is delayed and thus a gap continuously occurs in the sensor 111, the processor 130 may adjust the compression depth of the chest compressor 110 in the Z-axis direction.

Hereinafter, a method for searching an optimal chest compression site will be described in detail.

Figure 5:
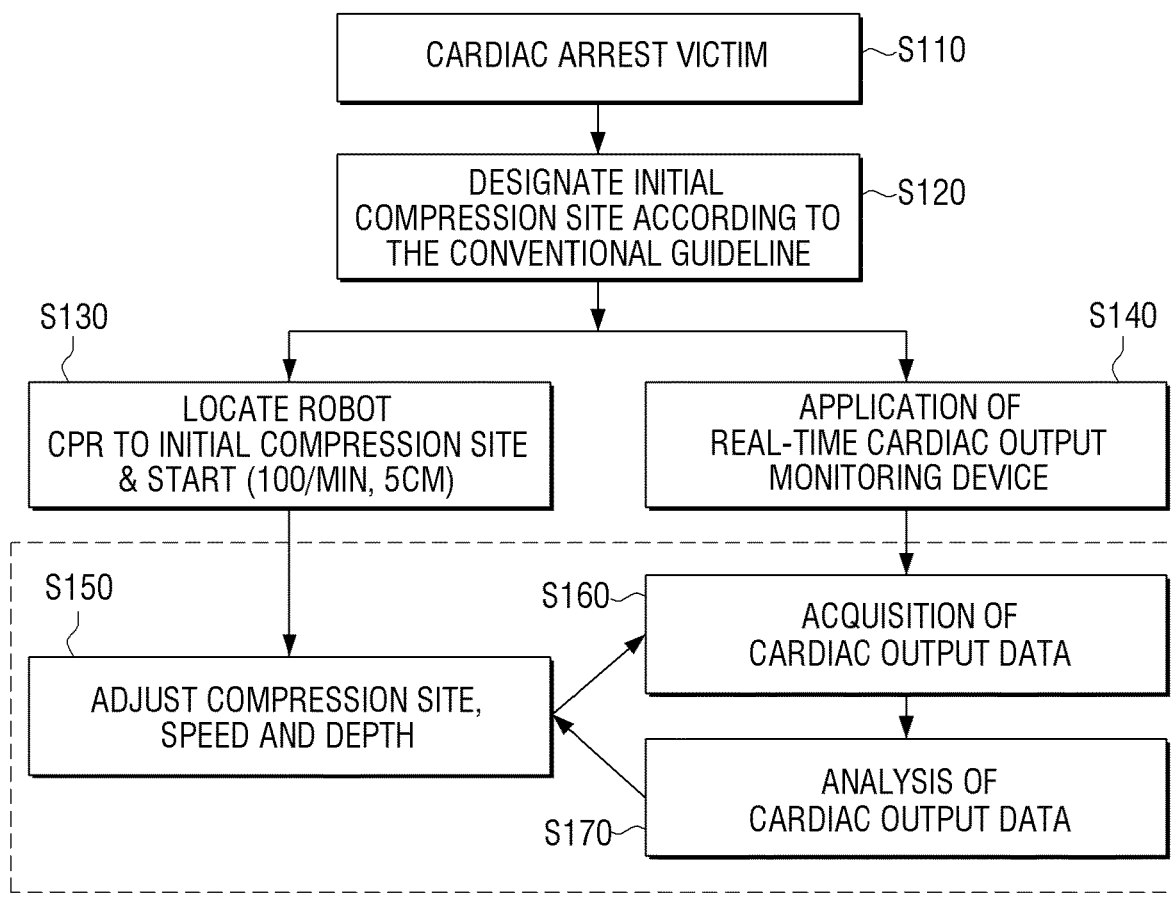
FIG. 5 is a view to illustrate an algorithm of the automatic cardiopulmonary resuscitation device according to an embodiment of the present disclosure.

FIG. 5 is a view illustrating an algorithm of an automatic cardiopulmonary resuscitation device according to an embodiment of the present disclosure.

When there is a cardiac arrest victim (S110), an initial compression site is designated according to the conventional guideline (S120). As described above, the guideline of the cardiopulmonary resuscitation indicates a middle point at which a line connecting victim's both nipples and the sternum meet. The initial compression site for chest compression may be manually selected by a medical team. Alternatively, when the automatic cardiopulmonary resuscitation device includes a camera, the automatic cardiopulmonary resuscitation device may photograph the victim's both nipples as an image, and may automatically search coordinates of an initial compression starting point based on the photographed image. The automatic cardiopulmonary resuscitation device may move down the chest compressor along the Z-axis, and may set a point at which a force is detected by the sensor as an initial compression point.

Operations of the automatic cardiopulmonary resuscitation device may be divided into a driving operation and a sensing operation. First, the automatic cardiopulmonary resuscitation device related to the driving operation places the chest compression robot on the initial compression site, and starts chest compression (S130). That is, the automatic cardiopulmonary resuscitation device controls the chest compressor located on the initial compression region to compress the chest according to the guideline (S130). For example, the guideline of the chest compression prescribes a cycle of about 100 times per minute and a depth of about 5 cm.

The automatic cardiopulmonary resuscitation device may include a device for monitoring cardiac output in real time. The device for monitoring cardiac output in real time may be referred to as a cardiac output measurement unit, and the cardiac output measurement unit in close contact with the victim measures cardiac output to analyze the quality of cardiopulmonary resuscitation. In addition, when the automatic cardiopulmonary resuscitation device 100 includes the bio signal measurement unit 150, the automatic cardiopulmonary resuscitation device 100 may also measure victim's bio signals, and may analyze the quality of cardiopulmonary resuscitation. The sensor 111 included in the automatic cardiopulmonary resuscitation device 100 measure a force and a torque which are generated as the compressing portion of the automatic cardiopulmonary resuscitation device 100 comes into contact with the victim in real time, and may transmit information on the force and the torque to the processor 130.

The automatic cardiopulmonary resuscitation device adjusts the compression site, speed (or cycle), and depth of the chest compressor based on cardiac output data (S150). The automatic cardiopulmonary resuscitation device may adjust the compression site by moving the chest compressor on the XY plane in the horizontal and vertical directions. In addition, the automatic cardiopulmonary resuscitation device may adjust the compression speed of the chest compressor by increasing or reducing the number of times of compressing per minute, and may adjust the compression depth by moving up or down the chest compressor on the Z-axis.

Next, the automatic cardiopulmonary resuscitation device related to the sensing operation may apply a real-time monitoring device (S140). The automatic cardiopulmonary resuscitation device acquires cardiac output data by using the real-time monitoring device (S160). For example, the automatic cardiopulmonary resuscitation device may include the cardiac output measurement unit and the bio signal measurement unit. The cardiac output measurement unit may measure cardiac output by using an ultrasound measurement method, an electrical bioimpedance cardiogram analysis method, capnography, a blood pressure waveform analysis method, or an intracardiac catheter method. In addition, the bio signal measurement unit may acquire bio signal data. For example, the bio signal may include blood oxygen saturation, end-tidal CO2, an electrocardiogram, or a blood pressure. As the blood oxygen saturation, the end-tidal CO2, the electrocardiogram, and the blood pressure increase within a predetermined range, the cardiac output increases. That is, the blood oxygen saturation, the end-tidal CO2, the electrocardiogram, and the blood pressure are in proportion to the cardiac output within the predetermined range.

The automatic cardiopulmonary resuscitation device analyzes the cardiac output data (S170). Alternatively, the automatic cardiopulmonary resuscitation device analyzes the cardiac output data based on the acquired cardiac output and the acquired bio signal. The automatic cardiopulmonary resuscitation device performs the processes of acquiring cardiac output data (S160), analyzing cardiac output data (S170), and adjusting the compression site, speed, and depth (S150) in real time. In addition, the results of the processes of acquiring cardiac output data (S160), analyzing cardiac output data (S170), and adjusting the compression site, speed, and depth (S150) may be mutually fed back. For example, when the automatic cardiopulmonary resuscitation device acquires and analyzes the cardiac output data, and then, when it is determined that cardiac output at a current compression site is less than cardiac output at a previous compression site, may move the chest compressor to the previous compression site. Alternatively, when it is determined that cardiac output at a current compression time is less than cardiac output at a previous compression time, the automatic cardiopulmonary resuscitation device may adjust the depth of the chest compressor. Alternatively, when it is determined that cardiac output in a current compression cycle (or speed) is insufficient, the automatic cardiopulmonary resuscitation device may adjust the cycle such that the chest compressor compresses the chest more frequently. In addition, the automatic cardiopulmonary resuscitation device may adjust the compression site, cycle, and depth in the reverse way to the above-described example.

Figure 6:
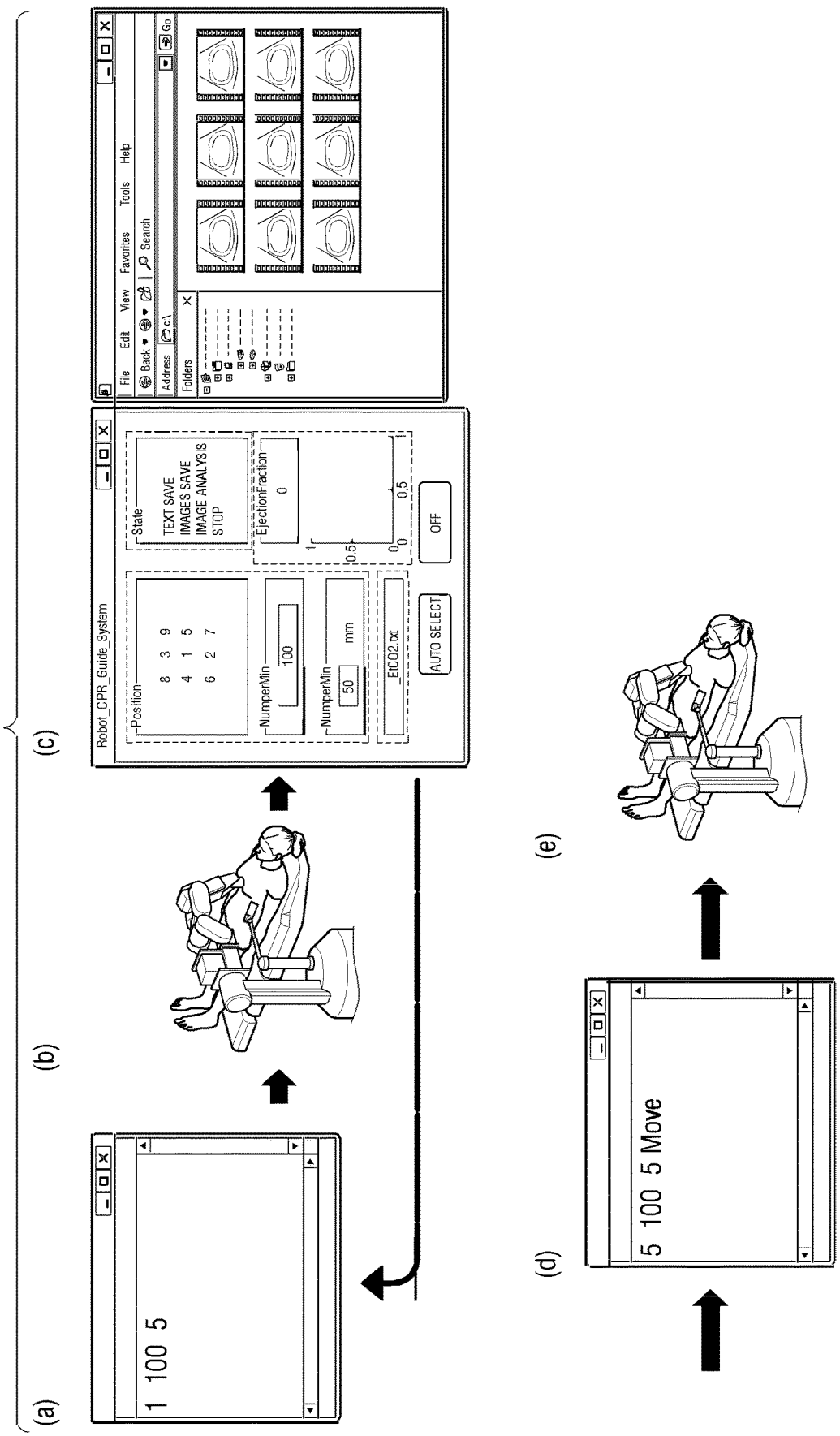
FIG. 6 is a view to illustrate an operating scenario of the automatic cardiopulmonary resuscitation device according to an embodiment of the present disclosure.

FIG. 6 is a view illustrating a driving scenario of an automatic cardiopulmonary resuscitation device according to an embodiment of the present disclosure.

Referring to FIG. 6(a), the automatic cardiopulmonary resuscitation device may receive an operating command from a user. In an embodiment, the automatic cardiopulmonary resuscitation device may display an input window through which compression site, cycle, and depth are inputted. The automatic cardiopulmonary resuscitation device may receive a command related to chest compression through the displayed input window. For example, as shown in FIG. 6(a), the automatic cardiopulmonary resuscitation device may receive a command of 1, 100, 5. The automatic cardiopulmonary resuscitation device may recognize the input command as indicating site number 1, 100 times per minute, and depth of 5 cm. The above-described example is an embodiment, and the input window and the command inputting method may be implemented in various ways.

Referring to FIG. 6(b), the automatic cardiopulmonary resuscitation device may perform a chest compression operation in response to the inputted command. The automatic cardiopulmonary resuscitation device may include a cardiac output measurement unit. Accordingly, the automatic cardiopulmonary resuscitation device may perform the chest compression operation at the same time as acquiring and analyzing cardiac output data through the cardiac output measurement unit. In addition, the automatic cardiopulmonary resuscitation device may further include a bio signal measurement unit, and may acquire bio signal data through the bio signal measurement unit. The automatic cardiopulmonary resuscitation device may calculate cardiac output by analyzing the acquired cardiac output data and bio signal data. For example, calculation of cardiac output may be indicated by ejection fraction (EF). The ejection fraction is a stroke volume of the left ventricle divided by an end-diastolic volume, and is one of the indexes indicating the pump function of the heart. As described above, the automatic cardiopulmonary resuscitation device may perform the operations of acquiring cardiac output data, acquiring bio signal data, analyzing cardiac output data, analyzing bio signal data, and adjusting compression in real time.

Referring to FIG. 6(c), the automatic cardiopulmonary resuscitation device may store the acquired cardiac output data and the acquired bio signal data, and may compare and display the analyzed ejection fraction and a value of the bio signal data. For example, the cardiac output data may be acquired by echocardiography. Accordingly, the cardiac output data may include an ultrasonographic image of the heart. In addition, the bio signal data may include end-tidal CO2 (EtCO2) partial pressure. Accordingly, the automatic cardiopulmonary resuscitation device may store heart's ultrasonographic image and the end-tidal CO2 partial pressure data. In addition, the automatic cardiopulmonary resuscitation device may store and display an image or data related to a blood pressure, an electrocardiogram, and blood oxygen saturation.

The automatic cardiopulmonary resuscitation device may perform the compression operation, while automatically changing the compression site. In addition, the automatic cardiopulmonary resuscitation device may acquire and analyze the cardiac output data and the bio signal data in real time at the same time as performing the compression operation. The automatic cardiopulmonary resuscitation device may automatically set optimal chest compression site, depth, and cycle based on the result of analyzing, and may perform the chest compression operation.

The automatic cardiopulmonary resuscitation device may perform the compression operation according to a user's command Referring to FIG. 6(d), a process of the automatic cardiopulmonary resuscitation device receiving a user's command is illustrated. In some cases, the automatic cardiopulmonary resuscitation device needs to perform a chest compression operation according to a determination of a medical team. Although the automatic cardiopulmonary resuscitation device may perform the chest compression operation according to the optimal chest compression site, depth, and cycle automatically determined, as described above, the automatic cardiopulmonary resuscitation device may perform the compression operation according to chest compression site, depth, and cycle corresponding to an inputted command of the medical team. For example, the medical team may determine that site number 5, 100 times per minutes, and depth of 5 cm are optimal for the chest compression operation, and may input a command of 5, 100, 5, move to the automatic cardiopulmonary resuscitation device.

Referring to FIG. 6(e), the automatic cardiopulmonary resuscitation device which performs the chest compression operation in response to the inputted command is illustrated. The automatic cardiopulmonary resuscitation device may move to site number 5 and perform the chest compression operation to the depth of 5 cm 100 times per minute in response to the inputted command of 5, 100, 5, move.

As described above, the automatic cardiopulmonary resuscitation device may perform the compression operation at various sites, and may acquire and analyze the cardiac output data and the bio signal data at the same time as performing the compression operation. In addition, the automatic cardiopulmonary resuscitation device may perform the chest compression operation according to various sites, depths, and cycles, and then may determine the optimal site, depth, and cycle. The automatic cardiopulmonary resuscitation device may move to the site that is determined as being optimal, and perform the chest compression operation according to the optimal depth and cycle. The automatic cardiopulmonary resuscitation device may display an input window to receive a command from the medical team. When a command related to the chest compression operation is inputted from the medical team, the automatic cardiopulmonary resuscitation device may perform the chest compression operation in response to the inputted command That is, the automatic cardiopulmonary resuscitation device may give a higher priority to the command related chest compression that is inputted by the medical team than setting related to the optimal chest compression operation that is determined by itself.

Hereinafter, an input interface for inputting a command to the automatic cardiopulmonary resuscitation device will be described.

Figure 7:
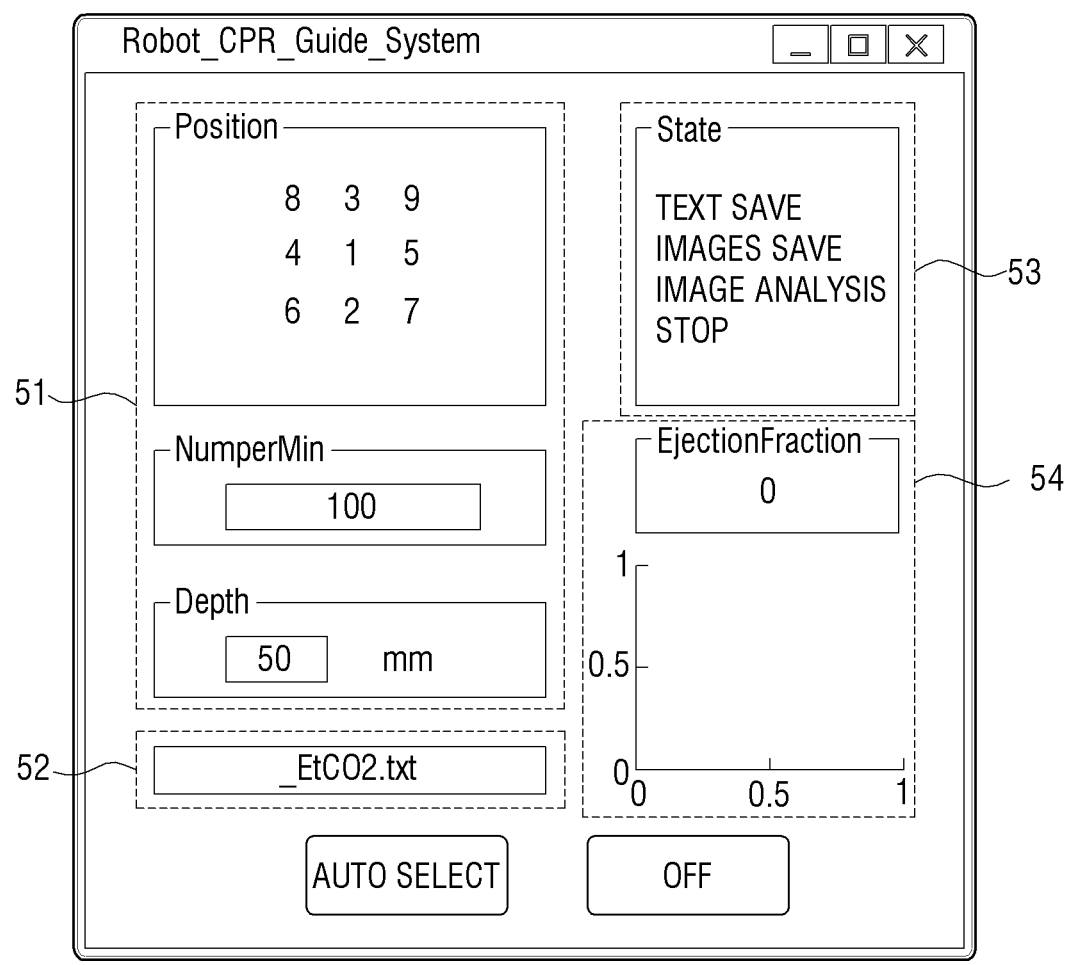
FIG. 7 is a view to illustrate a user interface according to an embodiment of the present disclosure.

FIG. 7 is a view illustrating a user interface according to an embodiment of the present disclosure.

Referring to FIG. 7, a user interface for inputting a command to the automatic cardiopulmonary resuscitation device is illustrated. The user interface may include an input region 51 for inputting a command to the automatic cardiopulmonary resuscitation device. For example, the input region 51 may receive input of values regarding compression site, cycle (or speed), and depth. The compression site may be displayed to correspond to a predetermined point. For example, sites of chest compression may be set to 9 points, and as shown in FIG. 7, numbers 1 to 9 may be displayed. When sites of chest compression are set to 15 points, numbers 1 to 15 may be displayed. The compression cycle may be inputted by number. For example, when 100 is inputted, the chest compression operation may be performed 100 times per minute. The compression depth may be inputted by number. For example, when 50 is inputted, the chest compression operation may be performed to the depth of 50 mm.

The user interface may include a region 52 indicating an end-tidal CO2 partial pressure (EtCO2) measurement file. As described above, the automatic cardiopulmonary resuscitation device may measure and store the end-tidal CO2 partial pressure. In addition, the automatic cardiopulmonary resuscitation device may display the region 52 indicating a measurement file of the end-tidal CO2 partial pressure or a path through which the measurement file is stored.

The user interface may include a current state display region 53. The current state may include storage of the end-tidal CO2 partial pressure data, storage of image data, analysis of image, stop, etc.

In addition, the user interface may include an ejection fraction (EF) display region 54. As described above, the ejection fraction is a stroke volume of the left ventricle divided by an end-diastolic volume, and is one of the indexes indicating the pump function of the heart. That is, the ejection fraction may be an index indicating cardiac output. The user interface may display a value of the ejection fraction in real time. Accordingly, a medical team may determine cardiac output caused by a current chest compression operation in real time, and may determine an optimal chest compression site.

In addition, the user interface may further include an automatic selection button, an off button, an end button, etc. The above-described example is an embodiment of the user interface, and the user interface may be implemented to have various regions and various shapes.

Hereinafter, a specific embodiment in which an automatic cardiopulmonary resuscitation device automatically changes a compression site and performs a chest compression operation, and determines an optimal chest compression site at which cardiac output becomes the maximum will be described.

FIGS. 8 to 13 are views to illustrate a process of searching an optimal compression site according to an embodiment of the present disclosure.

The automatic cardiopulmonary resuscitation device compresses a chest while moving the chest compressor according to a predetermined method, and simultaneously, measure cardiac output. In addition, the automatic cardiopulmonary resuscitation device determines a compression site at which cardiac output becomes the maximum as an optimal chest compression site, based on the measured cardiac output. The automatic cardiopulmonary resuscitation device moves the chest compressor to the chest compression site determined as being optimal, and performs a chest compression operation.

According to an embodiment, the automatic cardiopulmonary resuscitation device may set the compression site to 9 points in total including a combination of 3 points in the horizontal direction and 3 points in the vertical direction. The number of compression points is an embodiment, and various numbers of compression points may be set.

A predetermined method for the automatic cardiopulmonary resuscitation device to find an optimal chest compression site may be measuring victim's cardiac output while moving the chest compressor in the vertical direction. In addition, the automatic cardiopulmonary resuscitation device may select a first compression site at which the victim's cardiac output becomes the maximum, based on the measured cardiac output. The automatic cardiopulmonary resuscitation device compresses the chests at left and right compression sites of the selected first compression site, and also, measures cardiac output, and may select a compression site at which the cardiac output becomes the maximum as the optimal compression site. In general, when the periphery of the compression site at which the cardiac output becomes the maximum is compressed, more blood may be ejected than when other compression sites are compressed. Accordingly, the automatic cardiopulmonary resuscitation device compresses the chest along the vertical direction, first, and then compresses left and right sites of the compression site at which the cardiac output becomes the maximum, and measures cardiac output and determines the optimal compression site. According to an embodiment, the automatic cardiopulmonary resuscitation device may compress while moving by 2 cm at a time in the vertical direction and moving by 1 cm at a time in the horizontal direction.

Alternatively, the automatic cardiopulmonary resuscitation device may measure victim's cardiac output while moving the chest compressor in the horizontal direction. In addition, the automatic cardiopulmonary resuscitation device may select a first compression site at which the victim's cardiac output becomes the maximum, based on the measured cardiac output. The automatic cardiopulmonary resuscitation device compresses the chests at upper and lower compression sites of the selected first compression site, and also, measures cardiac output, and may select a compression site at which the cardiac output becomes the maximum as the optimal compression site. That is, the automatic cardiopulmonary resuscitation device compresses the chest along the horizontal direction, and then, compresses upper and lower sites of the compression site at which the cardiac output becomes the maximum, and measures cardiac output and determines the optimal compression site. According to an embodiment, the automatic cardiopulmonary resuscitation device may compress while moving by 2 cm at a time in the horizontal direction and moving by 1 cm at a time in the vertical direction.

Figure 8:
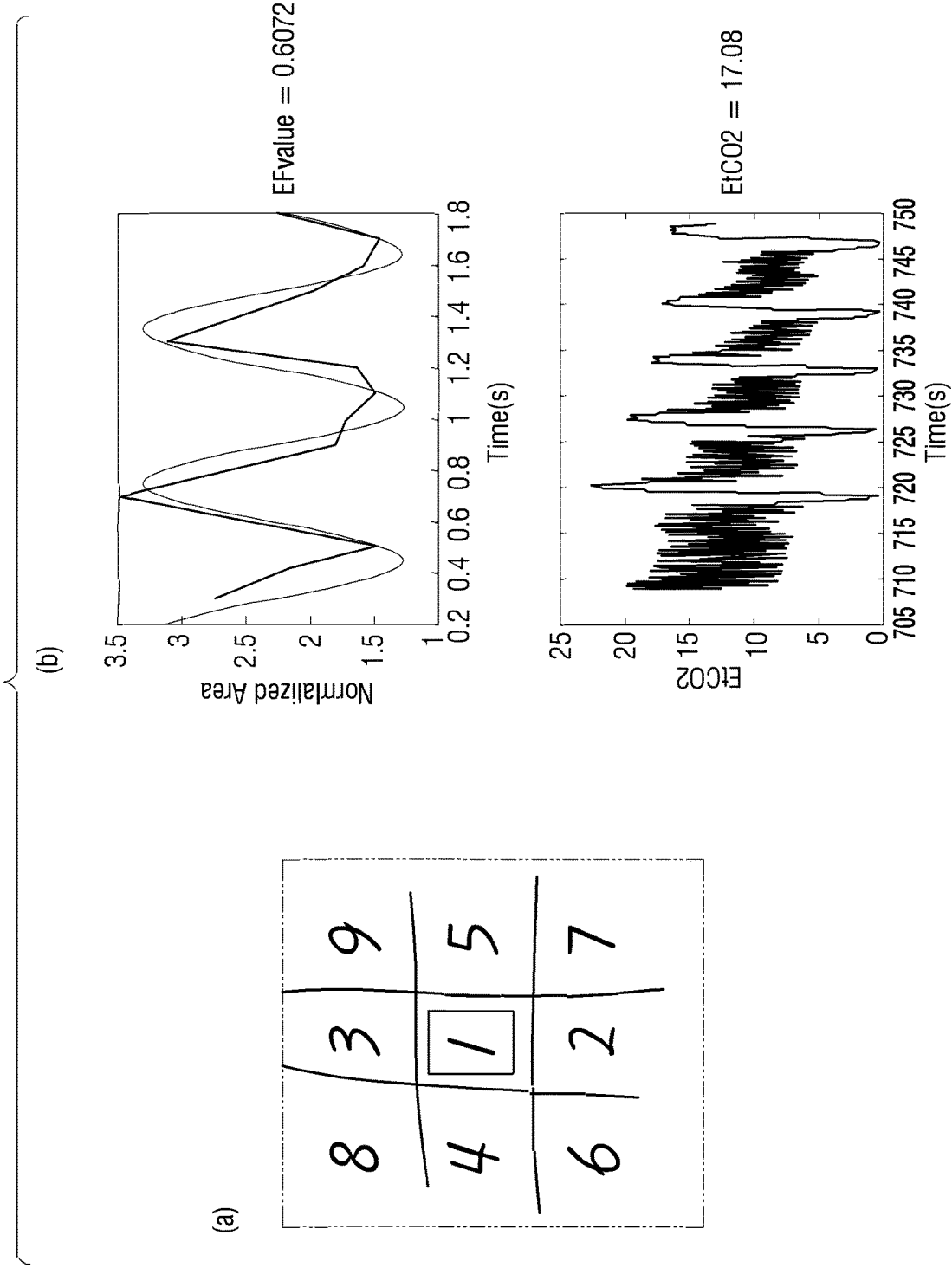
FIGS. 8 to 13 are views illustrating a process of searching an optimal compression site according to an embodiment of the present disclosure.

FIG. 8 is a view illustrating a process in which chest compression is performed at site number 1. 9 compression points are illustrated in FIG. 8(a). Initially, the automatic cardiopulmonary resuscitation device may compress the chest at site number 1. As described above, site number 1 may be a site following the guideline of the cardiopulmonary resuscitation. The chest compressor of the automatic cardiopulmonary resuscitation device may be moved to site number 1 by a medical team. Alternatively, the automatic cardiopulmonary resuscitation device may photograph victim's chest and may analyze the photographed image, and may move the chest compressor to site number 1. The automatic cardiopulmonary resuscitation device may compress the chest at site number 1. The automatic cardiopulmonary resuscitation device may compress the chest according to a compression depth and a compression cycle according to the guideline. In addition, the automatic cardiopulmonary resuscitation device may compress the chest at site number 1 for a predetermined time. For example, the automatic cardiopulmonary resuscitation device may compress the chest for about 3-4 minutes. This is because the automatic cardiopulmonary resuscitation device should measure cardiac output while compressing the chest for a predetermined time in order to determine the quality of chest compression. However, a time for keeping the chest compression to determine the quality of chest compression may be appropriately set. In addition, the automatic cardiopulmonary resuscitation device may compress the chest and measure cardiac output, while changing the compression site and the compression cycle. The automatic cardiopulmonary resuscitation device may perform chest compression for a predetermined time when compressing at other sites, and may compress the chest and measure cardiac output while changing the compression depth and the compression cycle.

FIG. 8(b) illustrates a signal measured while the chest is compressed at site number 1. For example, the automatic cardiopulmonary resuscitation device may measure cardiac output and end-tidal CO2 partial pressure (EtCO2), while compressing the chest. The automatic cardiopulmonary resuscitation device may determine the quality of chest compression based on the measured cardiac output and end-tidal CO2 partial pressure, and may select an optimal chest compression site. FIG. 8(b) illustrates ejection fraction (EF) and end-tidal CO2 partial pressure (EtCO2) measured while the automatic cardiopulmonary resuscitation device compresses the chest for a predetermined time. The ejection fraction is a measurement of cardiac output. In addition, the end-tidal CO2 partial pressure refers to the partial pressure of carbon dioxide included in exhaled gas of the victim, and is in proportion to the cardiac output.

Figure 9:
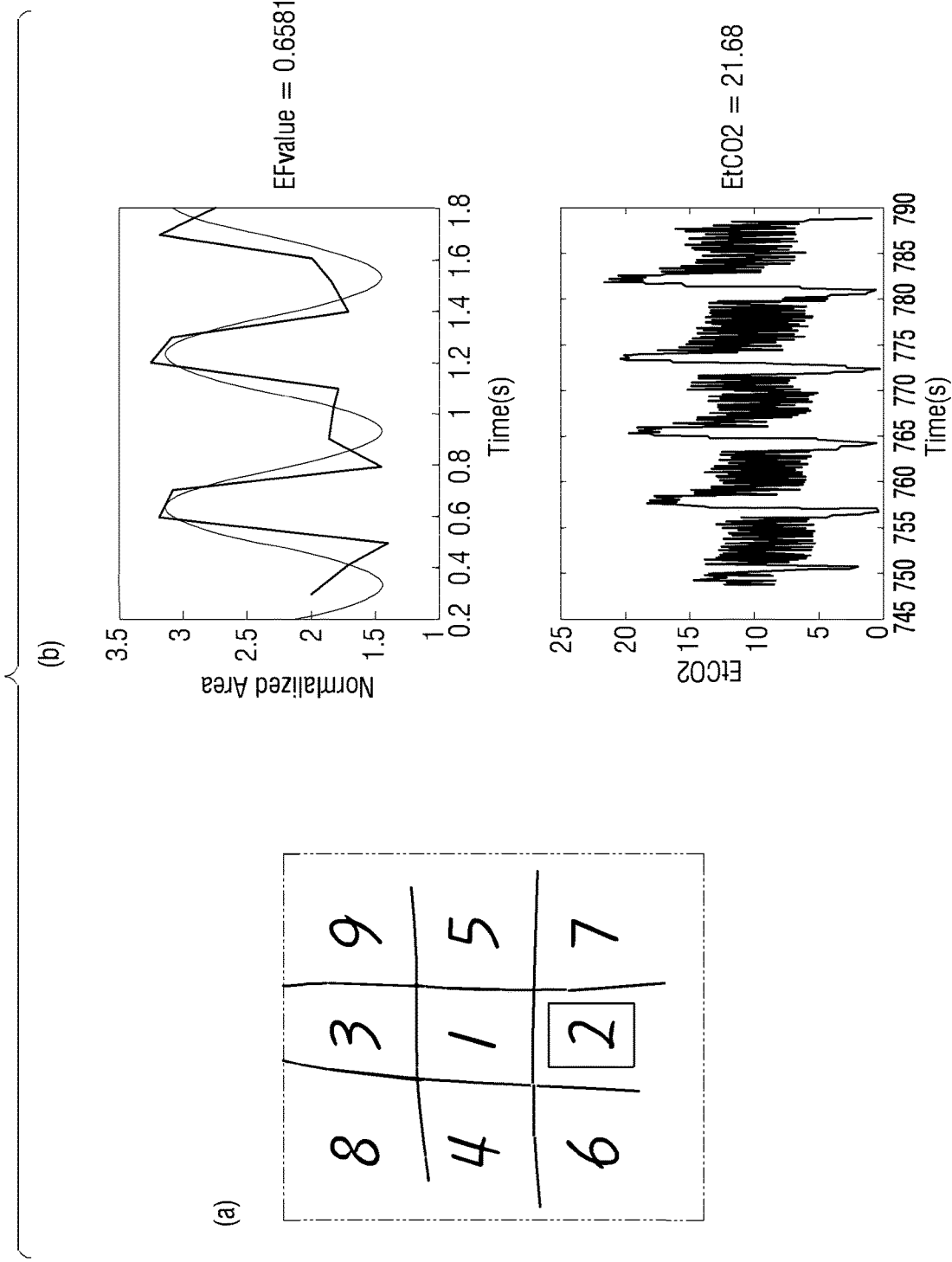

FIG. 9 is a view illustrating a process in which chest compression is performed at site number 2. 9 compression points are illustrated in FIG. 9(a). The automatic cardiopulmonary resuscitation device may compress the chest and may measure cardiac output and bio signals, while moving the chest compressor in the vertical direction. Site number 2 may be located on a lower side of site number 1. According to an embodiment, the automatic cardiopulmonary resuscitation device may move the chest compressor about 2 cm below site number 1, and may compress the chest.

FIG. 9(b) illustrates a signal measured while the chest is compressed at site number 2. The automatic cardiopulmonary resuscitation device may determine the quality of chest compression based on the measured cardiac output and end-tidal CO2 partial pressure. FIG. 9(b) illustrates ejection fraction (EF) and end-tidal CO2 partial pressure (EtCO2) measured while the automatic cardiopulmonary resuscitation device compresses the chest for a predetermined time. The ejection fraction (EF) and the end-tidal CO2 partial pressure (EtCO2) illustrated in FIG. 9(b) are larger than the ejection fraction (EF) and the end-tidal CO2 partial pressure (EtCO2) illustrated in FIG. 8(b). That is, site number 2 may be a more appropriate chest compression site than site number 1. The automatic cardiopulmonary resuscitation device may move the chest compressor in the vertical direction.

Figure 10:
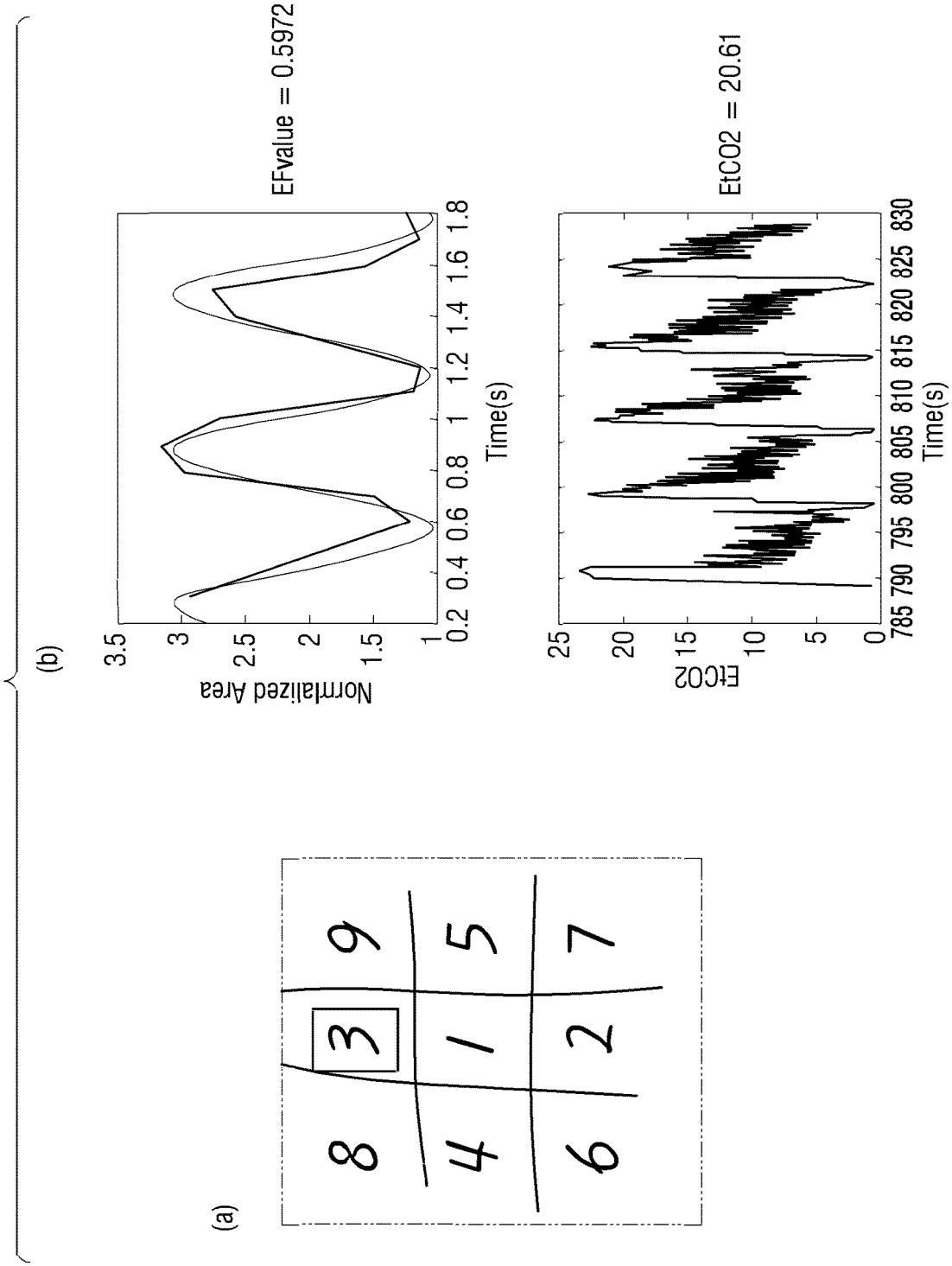

FIG. 10 is a view illustrating a process in which chest compression is performed at site number 3. 9 compression points are illustrated in FIG. 10(a). The automatic cardiopulmonary resuscitation device may compress the chest and may measure cardiac output and bio signals, while moving the chest compressor in the vertical direction. Site number 3 may be located on an upper side of site number 1. According to an embodiment, the automatic cardiopulmonary resuscitation device may move the chest compressor about 4 cm above site number 2, and may compress the chest. That is, site number 3 may be about 2 cm above site number 1, and may be about 4 cm above site number 2.

FIG. 10(b) illustrates a signal measured while the chest is compressed at site number 3. The automatic cardiopulmonary resuscitation device may determine the quality of chest compression based on the measured cardiac output and end-tidal CO2 partial pressure. FIG. 10(b) illustrates ejection fraction (EF) and end-tidal CO2 partial pressure (EtCO2) measured while the automatic cardiopulmonary resuscitation device compresses the chest for a predetermined time. The ejection fraction (EF) and the end-tidal CO2 partial pressure (EtCO2) illustrated in FIG. 10(b) are smaller than the ejection fraction (EF) and the end-tidal CO2 partial pressure (EtCO2) illustrated in FIG. 9(b). That is, site number 2 may be a more appropriate chest compression site than site number 3.

When the compression sites are 9 points, the automatic cardiopulmonary resuscitation device may compress the chest at the three points in the vertical direction, and may measure cardiac output. As shown in FIGS. 8 to 10, the automatic cardiopulmonary resuscitation device may determine that site number 2 is an appropriate compression point from among the three points, based on the measured cardiac output, etc. That is, site number 2 is a temporarily determined first compression point. The automatic cardiopulmonary resuscitation device may compress the chest at left and right points of the first compression point, that is, of site number 2, and may measure cardiac output.

Figure 11:
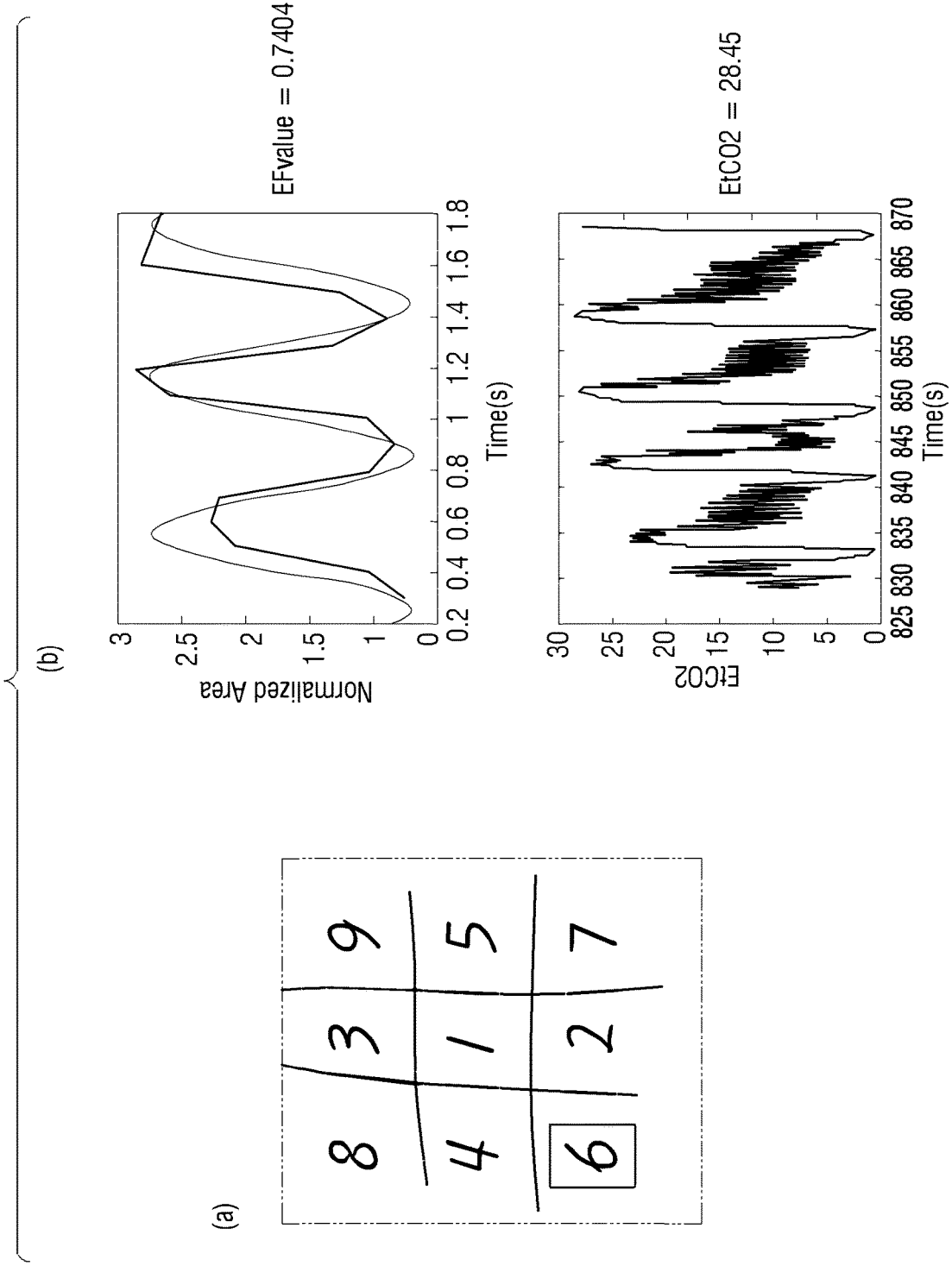

FIG. 11 is a view illustrating a process in which chest compression is performed at site number 6. 9 compression points are illustrated in FIG. 11(a). The automatic cardiopulmonary resuscitation device may compress the chest while moving the chest compressor in the directions of left and right (or in the horizontal direction) with reference to the first compression point, and may measure cardiac output and bio signals. In the present embodiment, the first compression point is site number 2. Site number 6 may be located on the left of site number 2. According to an embodiment, the automatic cardiopulmonary resuscitation device may move the chest compressor about 4 cm below from site number 3, and to the left by about 1 cm, and may compress the chest. That is, site number 6 may be located on the left about 1 cm away from site number 2.

FIG. 11(b) illustrates a signal measured while the chest is compressed at site number 6. The automatic cardiopulmonary resuscitation device may determine the quality of chest compression based on the measured cardiac output and end-tidal CO2 partial pressure. FIG. 11(b) illustrates ejection fraction (EF) and end-tidal CO2 partial pressure (EtCO2) measured while the automatic cardiopulmonary resuscitation device compresses the chest for a predetermined time. The ejection fraction (EF) and the end-tidal CO2 partial pressure (EtCO2) illustrated in FIG. 11(b) are larger than the ejection fraction (EF) and the end-tidal CO2 partial pressure (EtCO2) illustrated in FIG. 9(b). That is, site number 6 may be a more appropriate chest compression site than site number 2. The automatic cardiopulmonary resuscitation device may move the chest compressor to the right.

Figure 12:
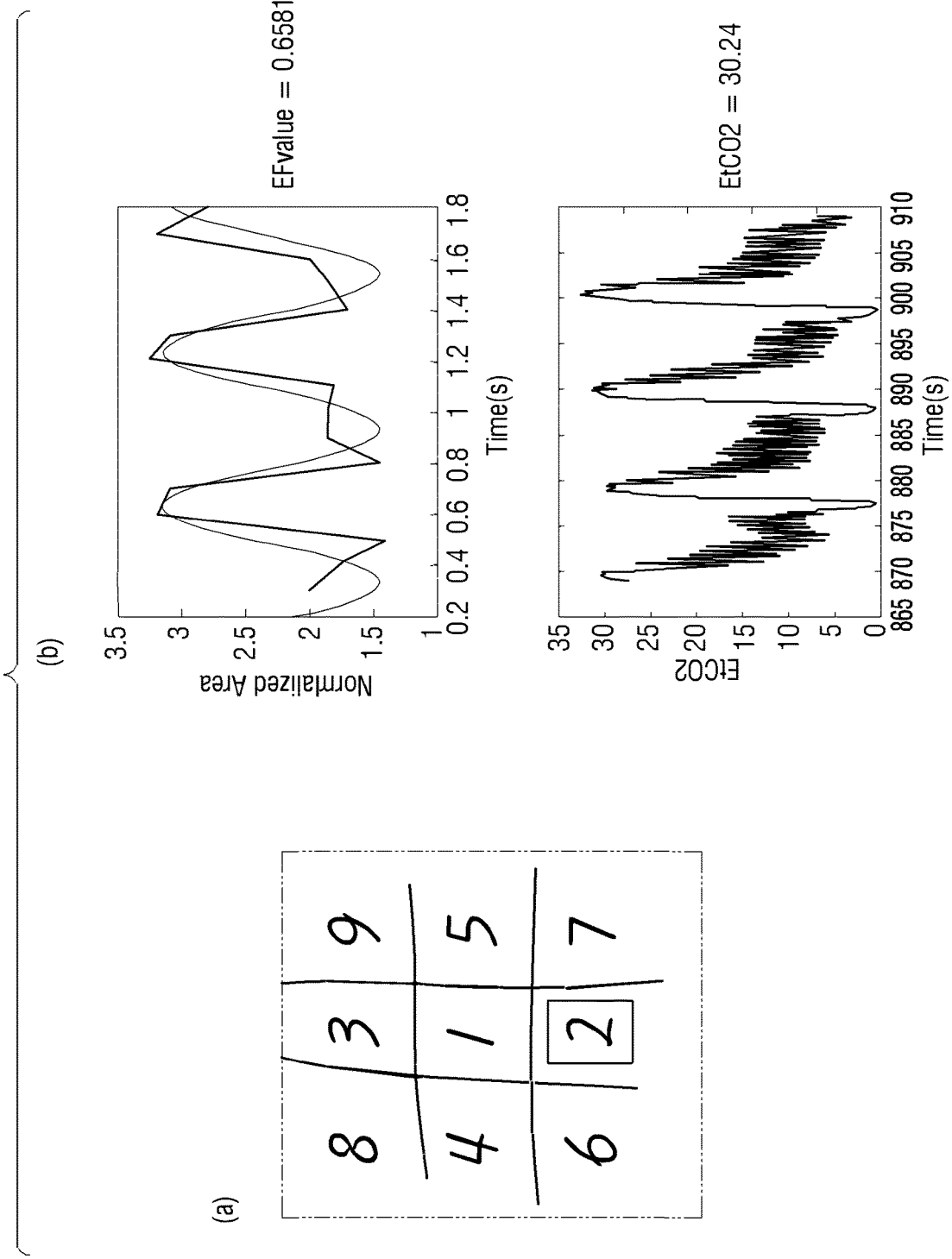

FIG. 12 is a view illustrating a process in which chest compression is performed at site number 2. 9 compression points are illustrated in FIG. 12(a). Site number 2 may be located on the right of site number 6. The automatic cardiopulmonary resuscitation device may move the chest compressor from site number 6 to the right by about 1 cm, and may compress the chest. That is, site number 2 may be located on the right about 1 cm away from site number 6. Since the chest compression at site number 2 has been previously performed, the automatic cardiopulmonary resuscitation device may omit the chest compression at site number 2, and may move to site number 7 and may perform the chest compression operation.

FIG. 12(b) illustrates a signal measured while the chest is compressed at site number 2. The automatic cardiopulmonary resuscitation device may determine the quality of chest compression based on the measured cardiac output and end-tidal CO2 partial pressure. FIG. 12(b) illustrates ejection fraction (EF) and end-tidal CO2 partial pressure (EtCO2) measured while the automatic cardiopulmonary resuscitation device compresses the chest for a predetermined time. The ejection fraction illustrated in FIG. 12(b) is smaller than the ejection fraction illustrated in FIG. 11(b). The end-tidal CO2 partial pressure illustrated in FIG. 12(b) is larger than the end-tidal CO2 partial pressure illustrated in FIG. 11(b). However, the end-tidal CO2 partial pressure may be used as auxiliary data for determining cardiac output. Accordingly, since the cardiac output at site number 6 is larger than the cardiac output at site number 2, site number 6 is still the more appropriate chest compression site. The automatic cardiopulmonary resuscitation device may move the chest compressor to the right.

Figure 13:
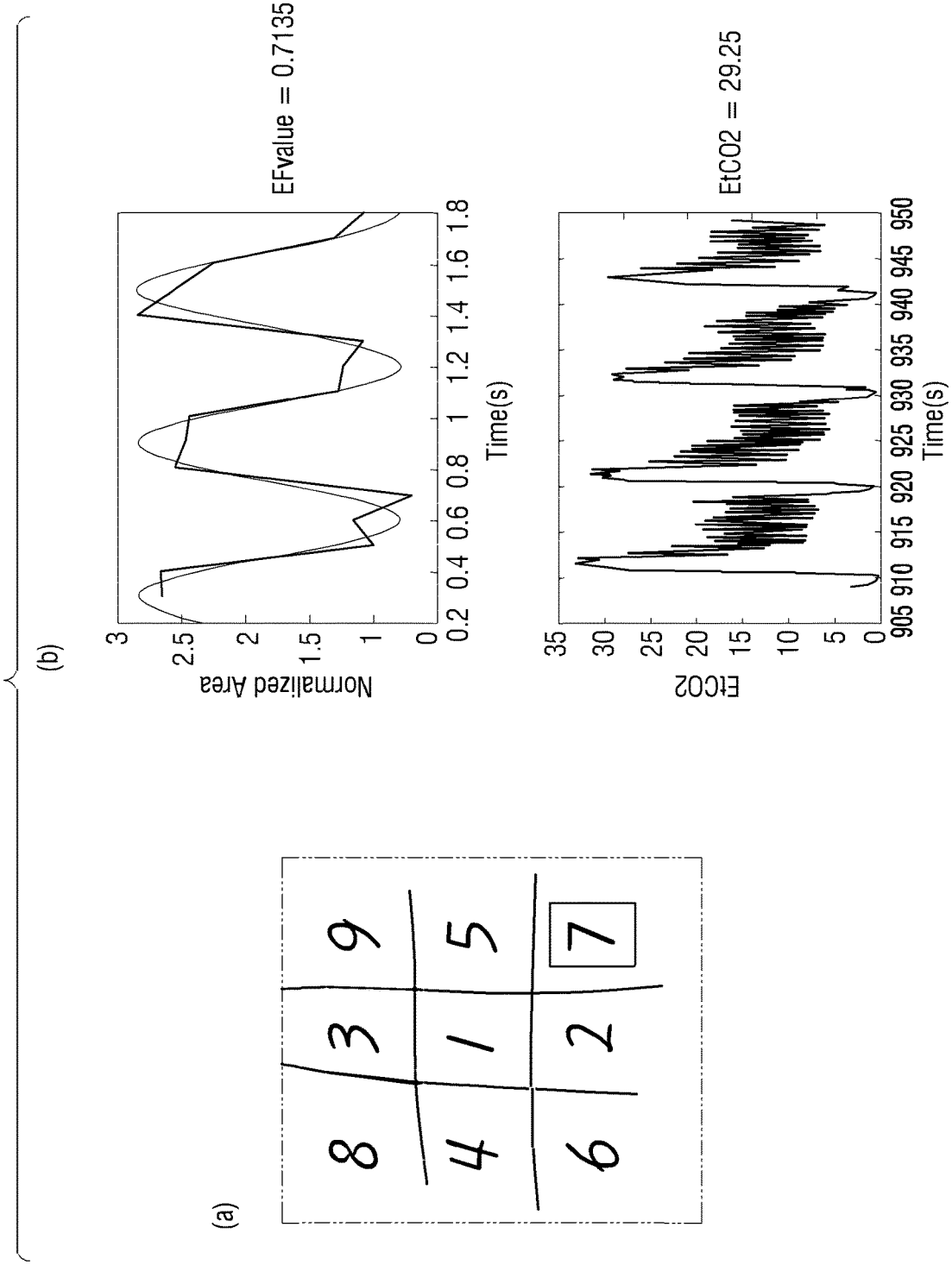

FIG. 13 is a view illustrating a process in which chest compression is performed at site number 7. 9 compression points are illustrated in FIG. 13(a). Site number 7 may be located on the right of site number 2. The automatic cardiopulmonary resuscitation device may move the chest compressor from site number 2 to the right by about 1 cm, and may compress the chest. That is, site number 7 may be located on the right about 1 cm away from site number 2.

FIG. 13(b) illustrates a signal measured while the chest is compressed at site number 7. The automatic cardiopulmonary resuscitation device may determine the quality of chest compression based on the measured cardiac output and end-tidal CO2 partial pressure. FIG. 13(b) illustrates ejection fraction (EF) and end-tidal CO2 partial pressure (EtCO2) measured while the automatic cardiopulmonary resuscitation device compresses the chest for a predetermined time. The ejection fraction illustrated in FIG. 13(b) is smaller than the ejection fraction illustrated in FIG. 11(b). The end-tidal CO2 partial pressure illustrated in FIG. 13(b) is larger than the end-tidal CO2 partial pressure illustrated in FIG. 11(b). However, the end-tidal CO2 partial pressure may be used as auxiliary data for determining cardiac output. In addition, since the cardiac output at site number 6 is larger than the cardiac output at site number 7, site number 6 is still the more appropriate chest compression site. Accordingly, since the automatic cardiopulmonary resuscitation device measures the maximum cardiac output when compressing at site number 6, the automatic cardiopulmonary resuscitation device may select site number 6 as the final optimal chest compression site. The automatic cardiopulmonary resuscitation device may move the chest compressor to the right.

The automatic cardiopulmonary resuscitation device may measure cardiac output at each point, while adjusting the chest compression cycle or depth. The automatic cardiopulmonary resuscitation device may select an optimal compression cycle or depth based on the measured cardiac output. That is, the automatic cardiopulmonary resuscitation device may compress the chest while changing the compression site, and may compress the chest and may measure cardiac output while adjusting the compression cycle or depth. In addition, the automatic cardiopulmonary resuscitation device may select the optimal compression site, compression cycle, and compression depth based on the measured cardiac output, and may perform the chest compression operation.

Up to now, the process of determining the optimal chest compression site, cycle, and depth has been described. Hereinafter, a control method of an automatic cardiopulmonary resuscitation device will be described.

Figure 14:
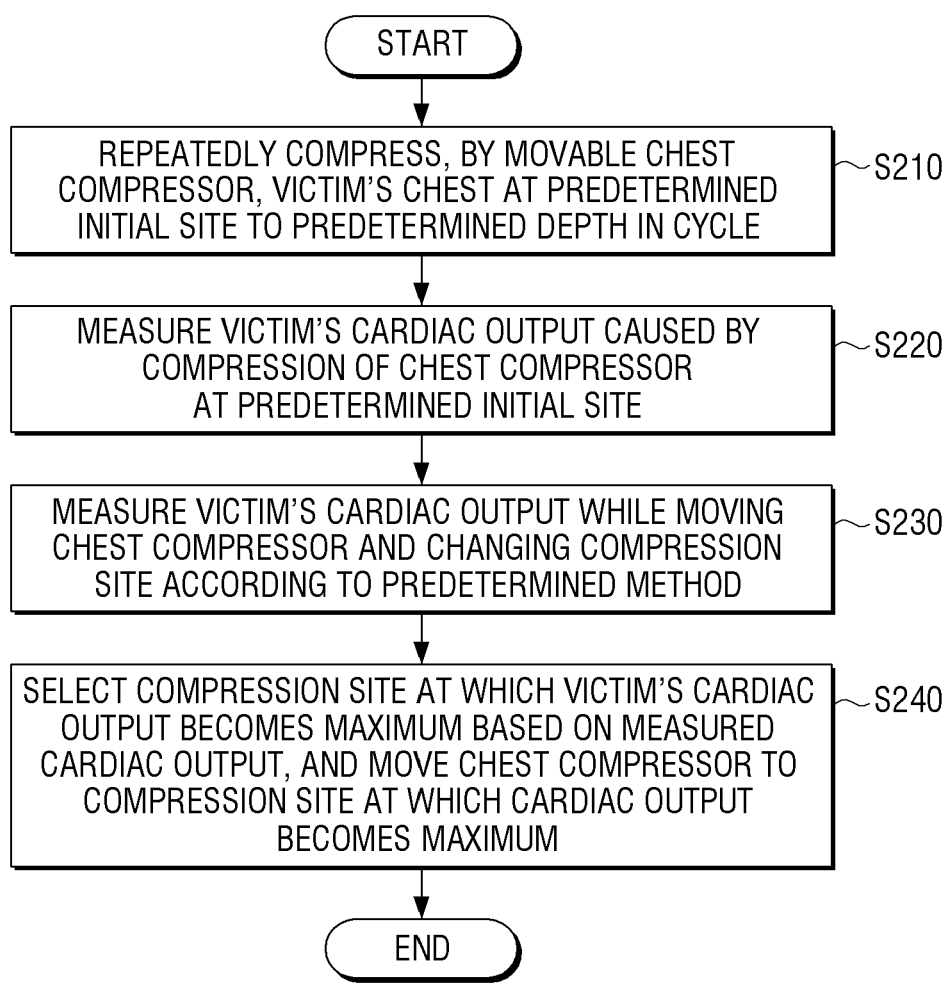
FIG. 14 is a flowchart of a method for controlling an automatic cardiopulmonary resuscitation device according to an embodiment of the present disclosure.

FIG. 14 is a flowchart of a control method of an automatic cardiopulmonary resuscitation device according to an embodiment of the present disclosure.

Referring to FIG. 14, the automatic cardiopulmonary resuscitation device repeatedly compresses victim's chest at a predetermined initial site according to predetermined depth and cycle by using a movable chest compressor (S210). The predetermined initial site, and the predetermined depth and cycle may follow the guideline. That is, the predetermined initial site may be a middle point at which a line connecting victim's both nipples and the sternum meet, the predetermined depth is 5 cm or more, and the predetermined cycle may be 100 times or more per minute. The chest compressor of the automatic cardiopulmonary resuscitation device may be moved by a medical team, or may be automatically moved based on a photographed image.

The automatic cardiopulmonary resuscitation device may measure victim's cardiac output caused by the compression of the chest compressor at the predetermined initial site (S220). The automatic cardiopulmonary resuscitation device may include a cardiac output measurement unit to measure cardiac output in various methods. In addition, the automatic cardiopulmonary resuscitation device may include a bio signal measurement unit to measure various bio signals. The automatic cardiopulmonary resuscitation device may determine the quality of chest compression on a compressed portion based on the measured cardiac output. Alternatively, the automatic cardiopulmonary resuscitation device may determine the quality of chest compression on the compressed portion based on the measured cardiac output and the measured bio signals. The automatic cardiopulmonary resuscitation device may use the measured bio signals as auxiliary data for determining the quality of chest compression.

The automatic cardiopulmonary resuscitation device may measure the victim's cardiac output while changing the compression site by moving the chest compressor according to a predetermined method (S230). For example, the automatic cardiopulmonary resuscitation device may measure victim's cardiac output while moving the chest compressor in one direction of the horizontal direction or the vertical direction, and may select a first compression site at which the victim's cardiac output becomes the maximum, based on the measured cardiac output. In addition, the automatic cardiopulmonary resuscitation device may measure cardiac output, while compressing the chest at a second compression site and a third compression site, which are on both sides with reference to the first compression site in a direction perpendicular to the moving direction of the chest compressor.

The automatic cardiopulmonary resuscitation device may select a compression site at which the victim's cardiac output becomes the maximum, based on the measured cardiac output, and may move the chest compressor to the compression site at which the cardiac output becomes the maximum (S240). The automatic cardiopulmonary resuscitation device may select the compression site at which the victim's cardiac output becomes the maximum as the final compression site, based on the cardiac output measured at the first to third compression sites. The automatic cardiopulmonary resuscitation device may move the chest compressor to the final compression site, and may compress the chest.

The control method of the automatic cardiopulmonary resuscitation device according to the above-described various embodiments may be implemented as a program, and may be provided to the automatic cardiopulmonary resuscitation device. For example, a non-transitory computer readable medium in which the program for performing the control method of the automatic cardiopulmonary resuscitation device is stored may be provided.

The non-transitory computer readable medium refers to a medium that stores data semi-permanently rather than storing data for a very short time, such as a register, a cache, and a memory, and is readable by an apparatus. Specifically, the above-described applications or programs may be stored in a non-transitory computer readable medium, such as a CD-ROM, a digital versatile disk (DVD), a hard disk, a Blu-ray disk, a universal serial bus (USB), a memory card, and a read only memory (ROM), or the like, and may be provided.

According to embodiments of the present disclosure, the automatic cardiopulmonary resuscitation device automatically selects an optimal chest compression site, and the chest compressor rapidly and exactly moves to that site, such that chest compression can be continuously performed according to optimal depth and speed without causing fatigue and interruption.

Accordingly, a medical team can observe important states of a victim during cardiopulmonary resuscitation, and can focus on providing an appropriate treatment. Therefore, efficiency of treatment of a cardiac arrest can be enhanced. Furthermore, automated cardiopulmonary resuscitation using a robot can be performed in an ambulance or an emergency site as well as hospitals, and thus there is an effect that a survival rate of a victim having a cardiac arrest is noticeably enhanced.

While preferred embodiments of the present disclosure have been illustrated and described, the present disclosure is not limited to the above-described specific embodiments. Various changes can be made by a person skilled in the art without departing from the scope of the present disclosure claimed in claims, and also, changed embodiments should not be understood as being separate from the technical idea or prospect of the present disclosure.

What is claimed is:

1. An automatic cardiopulmonary resuscitation device, comprising:
   a chest compressor which is movable, and is configured to repeatedly compress a victim's chest to a predetermined depth and in a predetermined cycle;
   a cardiac output measurement unit configured to measure a cardiac output of the victim caused by compression of the chest compressor; and
   a processor configured to control the chest compressor to move according to a predetermined method, and to change a compression site,
   wherein the processor is configured to control the cardiac output measurement unit to measure the cardiac output of the victim at each of the changed compression site, to select a compression site at which the cardiac output of the victim becomes the maximum among the measured cardiac output, and to control the chest compressor to move to the compression site at which the cardiac output of the victim becomes the maximum.

2. The automatic cardiopulmonary resuscitation device of claim 1, wherein the predetermined method is a method which measures the cardiac output of the victim while moving the chest compressor in one direction of a horizontal direction or a vertical direction, selects a first compression site at which the cardiac output of the victim becomes the maximum, based on the measured cardiac output, and to move the chest compressor to a second compression site and a third compression site which are on both sides of the first compression site in a direction perpendicular to the one direction of the chest compressor.

3. The automatic cardiopulmonary resuscitation device of claim 2, wherein the processor is configured to select a compression site at which the cardiac output of the victim becomes the maximum as a final compression site, based on cardiac outputs measured at the first to third compression sites.

4. The automatic cardiopulmonary resuscitation device of 1, wherein the processor is configured to control at least one of a compression site, a compression depth, or a compression cycle of the chest compressor to make the cardiac output of the victim become the maximum.

5. The automatic cardiopulmonary resuscitation device of 1, wherein the cardiac output measurement unit is configured to measure the cardiac output of the victim, by using at least one of an ultrasound measurement method, an electrical bioimpedance cardiogram analysis method, capnography, a blood pressure waveform analysis method, or an intracardiac catheter method.

6. The automatic cardiopulmonary resuscitation device of 1, further comprising a camera configured to photograph a chest of the victim,
wherein the processor is configured to determine a compression site of the chest compressor based on an image photographed by the camera.

7. The automatic cardiopulmonary resuscitation device of 1, further comprising a sensor configured to measure a pressure of the chest compressor compressing the victim.

8. The automatic cardiopulmonary resuscitation device of 1, further comprising a bio signal measurement unit configured to measure a bio signal of the victim,
wherein the processor is configured to determine whether a current compression site compressed by the chest compressor is an optimal compression site, based on the bio signal measured by the bio signal measurement unit.

9. The automatic cardiopulmonary resuscitation device of 8, wherein the bio signal comprises at least one of a blood pressure, an electrocardiogram, end-tidal $CO_2$, or blood oxygen saturation.

* * * * *